United States Patent
Elfar et al.

(10) Patent No.: US 9,993,429 B2
(45) Date of Patent: Jun. 12, 2018

(54) COMPOSITION AND METHODS FOR THE TREATMENT OF PERIPHERAL NERVE INJURY

(71) Applicant: UNIVERSITY OF ROCHESTER, Rochester, NY (US)

(72) Inventors: John Elfar, Rochester, NY (US); Kuang-Ching Tseng, Rochester, NY (US); Mark Noble, Brighton, NY (US)

(73) Assignee: University of Rochester, Rochester, NY (US)

( * ) Notice: Subject to any disclaimer, the term of this patent is extended or adjusted under 35 U.S.C. 154(b) by 0 days. days.

(21) Appl. No.: 14/777,080

(22) PCT Filed: Mar. 13, 2014

(86) PCT No.: PCT/US2014/026388
§ 371 (c)(1),
(2) Date: Sep. 15, 2015

(87) PCT Pub. No.: WO2014/151752
PCT Pub. Date: Sep. 25, 2014

(65) Prior Publication Data
US 2016/0038419 A1 Feb. 11, 2016

Related U.S. Application Data

(60) Provisional application No. 61/793,360, filed on Mar. 15, 2013.

(51) Int. Cl.
| | | |
|---|---|---|
| *A61K 9/16* | (2006.01) | |
| *A61K 31/4409* | (2006.01) | |
| *A61K 9/00* | (2006.01) | |
| *A61K 47/34* | (2017.01) | |
| *A61K 9/70* | (2006.01) | |
| *A61K 45/06* | (2006.01) | |

(52) U.S. Cl.
CPC .......... *A61K 9/1647* (2013.01); *A61K 9/0024* (2013.01); *A61K 9/7007* (2013.01); *A61K 31/4409* (2013.01); *A61K 45/06* (2013.01); *A61K 47/34* (2013.01)

(58) Field of Classification Search
CPC .. A61K 31/4409; A61K 9/0024; A61K 45/06; A61K 9/1647
USPC ........................................................ 424/489
See application file for complete search history.

(56) References Cited

U.S. PATENT DOCUMENTS

| | | | |
|---|---|---|---|
| 6,503,931 | B1 | 1/2003 | Meythaler |
| 6,855,331 | B2 | 2/2005 | Vook et al. |
| 8,007,826 | B2 | 8/2011 | Blight et al. |
| 8,354,437 | B2 | 1/2013 | Blight et al. |
| 8,367,116 | B2 | 2/2013 | Pratt et al. |
| 8,440,703 | B2 | 5/2013 | Blight et al. |
| 2005/0228030 | A1* | 10/2005 | Blight ............... A61K 31/44 514/352 |
| 2010/0015228 | A1 | 1/2010 | Lichter et al. |
| 2010/0021422 | A1* | 1/2010 | Temple ............... A61K 9/0019 424/85.2 |
| 2011/0166189 | A1 | 7/2011 | Blight et al. |
| 2011/0217264 | A1* | 9/2011 | Temple ............... A61K 9/0019 424/85.2 |
| 2012/0164078 | A1 | 6/2012 | Blight et al. |

FOREIGN PATENT DOCUMENTS

| | | |
|---|---|---|
| EP | 1535065 | 7/2007 |
| WO | 03103608 | 7/2004 |
| WO | 2008023725 | 2/2008 |

OTHER PUBLICATIONS

Rubin, Titled: Overview of peripheral nervous system disorders, Merck Manual, pp. 1-9, downloaded from https//www.merckmanuals.pdf on Apr. 26, 2016.*
Title: Sciatic nerve injury, Merck manual, downloaded from https//www.merckmanuals.pdf on Apr. 26, 2016.*
Definition of co-administration, Medical Dictionary by Merriam-Webster downloaded from http://www.merriam-webster.com/medical/coadministration on Apr. 27, 2016.*
Lymangrover et al; title: Effects of extracellular potassium and 4-aminopyridine on corticosteroid secretion, Molecular and Cellular Endocrinology;vol. 21, Issue 3, Mar. 1981, pp. 199-210.*
Pilar Martinez de Albornoz et al; Title: Non-surgical therapies for peripheral nerve injury; Br Med Bull (2011), pp. 1-28, First published online: Mar. 23, 2011.*
Dammers JW et al.; title: Injection with methylprednisolone proximal to the carpal tunnel: randomised double blind trial; BMJ. Oct. 2, 1999;vol. 319(7214), pp. 884-886.*
Berkingali et al., Neurite outgrowth on Cultured Spiral Ganglion Neurons Indeuced by Erythropoietin. Hearing Research 243, 2008, pp. 121-126.
Bever et al., Sustained-release fampridine for multiple sclerosis, Expert Opin Investig Drugs, vol. 18, No. 7, Jul. 31, 2009, pp. 1013-1024.
Bianchi et al., Erythropoietin Both Protects from and Reverses Experimental Diabetic Neuropathy. Proceedings of the National Academy of Sciences of the United Stated of America 101, 2004, pp. 823-828.
Bizzozero et al., Exposure of Rat Optic Nerves to Nitric Oxide Causes Protein S-Nitrosation and Myelin Decompaction. Neurochemical Research 29, 2004, pp. 1675-1685.

(Continued)

*Primary Examiner* — Yanzhi Zhang
(74) *Attorney, Agent, or Firm* — Kilpatrick Townsend & Stockton LLP

(57) ABSTRACT

Provided herein are methods of treating a peripheral nerve injury in a subject. The methods include administering to the subject at or near the site of the peripheral nerve injury an effective amount of a composition comprising an agent that promotes remyelination of the peripheral nerve. Also provided are methods of determining whether a peripheral nerve injury has a capacity for recovery. The methods include selecting a subject with a peripheral nerve injury, administering to the subject a first dose of a composition comprising and agent that promote remyelination and detecting after the first dose one or more characteristics of peripheral nerve recovery, the presence of one or more characteristics of peripheral nerve recovery indicating a peripheral nerve injury has a capacity for recovery and the absence of characteristics of peripheral nerve recovery indicating a peripheral nerve injury without a capacity for recovery.

9 Claims, 18 Drawing Sheets

(56) References Cited

OTHER PUBLICATIONS

Campana et al., Erythropoietin and erythropoietin receptors in the peripheral nervous system: changes after nerve injury. FASEB journal: official publication of the Federation of American Societies for Experimental Biology 15, 2001, 1804-1806.

Campana et al., Erythropoietin reduces Schwann cell TNF-alpha, Wallerian degeneration and pain-related behaviours after peripheral nerve injury. The European journal of neuroscience 23, 2006, pp. 617-626.

Campana et al., Exogenous erythropoietin protects against dorsal root ganglion apoptosis and pain following peripheral nerve injury. The European journal of neuroscience 18, 2003, pp. 1497-1506.

Conti et al., Inducible nitric oxide synthase (iNOS) in immune-mediated demyelination and Wallerian degeneration of the rat peripheral nervous system. Exp Neurol 187, 2004, pp. 350-358.

De Medinaceli et al., An index of the functional condition of rat sciatic nerve based on measurements made from walking tracks. Expo Neurol 77, 1982, pp. 634-343.

Elfar et al., Erythropoietin accelerates functional recovery after peripheral nerve injury. The Journal of Bone and Joint surgery American. vol. 90, 2008, pp. 1644-1653.

Facio et al., Penile rehabilitation and neuromodulation. TheScientificWorldJournal 9, 2009, pp. 652-664.

Gladman et al., Improved outcome after peripheral nerve injury in mice with increased levels of endogenous omega-3 polyunsaturated fatty acids. The Journal of neuroscience : the official journal of the Society for Neuroscience 32, 2012, pp. 563-571.

Iwai et al., Enhanced oligodendrogenesis and recovery of neurological function by erythropoietin after neonatal hypoxic/ischemic brain injury. Stroke; a journal of cerebral circulation 41, 2010, pp. 1032-1037.

Jehle et al., [Erythropoietin protects retinal ganglion cells and visual function after ocular ischemia and optic nerve compression]. Der Ophthalmologe : Zeitschrift der Deutschen Ophthalmologischen Gesellschaft 107, 2010, pp. 347-353.

Juul , Erythropoietin in the central nervous system, and its use to prevent hypoxic-ischemic brain damage. Acta paediatrica 91, 2002, pp. 36-42.

Keswani et al., A Novel Endogenous Erythropoietin Mediated Pathway Prevents Axonal Degeneration, vol. 56, No. 6, Dec. 2004, pp. 815-826.

Knowles et al., Nitric oxide synthases in mammals. The Biochemical journal 298 ( Pt 2), 1994, pp. 249-258.

Koeppen et al., Wallerian degeneration: history and clinical significance. Journal of the neurological sciences 220, 2004, pp. 115-117.

Lehmann et al., Role of nitric oxide as mediator of nerve injury in inflammatory neuropathies. Journal of neuropathology and experimental neurology 66, 2007, pp. 305-312.

Li et al., Schwann cells express erythropoietin receptor and represent a major target for Epo in peripheral nerve injury. Glia 51, 2005, pp. 254-265.

Maiese et al., Erythropoietin and oxidative stress. Current neurovascular research 5, 2008, pp. 125-142.

Noble et al., Analysis of upper and lower extremity peripheral nerve injuries in a population of patients with multiple injuries. The Journal of trauma 45, 1998, pp. 116-122.

International Patent Application No. PCT/US2014/026388 , International Preliminary Report on Patentability, dated Sep. 24, 2015, 7 Pages.

International Patent Application No. PCT/US2014/026388 , International Search Report and Written Opinion, dated Jul. 23, 2014, 14 pages.

Peeter et al., Effect of recombinant human erythropoietin on anaemia and disease activity in patients with rheumatoid arthritis and anaemia of chronic disease: a randomised placebo controlled double blind 52 weeks clinical trial. Annals of the rheumatic diseases 55, 1996, pp. 739-744.

Remuzzi et al., Correction of anemia—payoffs and problems. The New England journal of medicine 355, 2006, pp. 2144-2146.

Schmidt et al., Neural tissue engineering: strategies for repair and regeneration. Annual review of biomedical engineering 5, 2003, pp. 293-347.

Sears et al., The Effects of 4-Aminopyridine and Tetraethylammonium Ions on Normal and Demyelinated Mammalian Nerve Fibres, J. Physiol., 1981, 313:301-315.

Sherratt et al., Effects of 4-aminopyridine on normal and demyelinated mammalian nerve fibres. Nature 283, 1980, pp. 570-572.

Shi et al., Differential Effect of Low and High Concentrations of 4-Aminopyridine on Axonal Conduction in Normal and Injured Spinal Cord, Neuroscience vol. 77, No. 2, 1997, 10 pages.

Smith et al., The cardiovascular effects of erythropoietin. Cardiovasc Res 59, 2003, pp. 538-548.

Spicer et al., Fibrin glue as a drug delivery system. Journal of controlled release : official journal of the Controlled Release Society 148, 2010, pp. 49-55.

Stendel et al., Taurolidine-Fibrin-Sealant-Matrix using spray application for local treatment of brain tumors. Anticancer research 24, 2004, pp. 631-638.

Syed et al., Soluble neuregulin-1 has bifunctional, concentration-dependent effects on Schwann cell myelination. The Journal of neuroscience : the official journal of the Society for Neuroscience 30, 2010, pp. 6122-6131.

Vitellaro-Zuccarello et al., Erythropoietin-mediated preservation of the white matter in rat spinal cord injury. Neuroscience 144, 2007, pp. 865-877.

Waxman , Muscle & Nerve Journal, vol. 8, Issue 2, Feb. 1985, pp. 85-92.

Wu et al., Antioxidant effect of erythropoietin on 1-methyl-4-phenylpyridinium-induced neurotoxicity in PC12 cells. European journal of pharmacology 564, 2007, pp. 47-56.

Yin et al., Erythropoietin promotes functional recovery and enhances nerve regeneration after peripheral nerve injury in rats. AJNR American journal of neuroradiology 31, 2010, pp. 509-515.

Zielasek et al., Administration of nitric oxide synthase inhibitors in experimental autoimmune neuritis and experimental autoimmune encephalomyelitis. Journal of neuroimmunology 58, 1995, pp. 81-88.

* cited by examiner 4-aminopyridine         3,4-diaminopyridine

| Particle Fabrication | Homogenization Speed | | Homogenization Time | | Solidification of Particles | |
|---|---|---|---|---|---|---|
| | 1st: 21,000 rpm 2nd: 13,500 rpm | 1st: 17,500 rpm 2nd: 9,500 rpm | 30 sec | 90 sec | 1st: 21,000 rpm 2nd: 13,500 rpm w/ vacuum | 1st: 21,000 rpm 2nd: 13,500 rpm w/o vacuum |
| Encapsulation Capacity (µg 4AP/mg PLGA) | 0.8 - 1.2 | 0.5 - 0.8 | 0.8 - 1 | 1 - 1.2 | 0.1 - 0.3 | 0.8 - 1 |
| Shape or Size of the beads | N/A | Too fragile; broken spheres | 0.5 - 4 µm | 0.2 - 0.5 µm | Pores on shell | 0.5 - 4 µm |
*FIG. 4A*
*FIG. 4B*
*FIG. 4C*
*FIG. 4D*

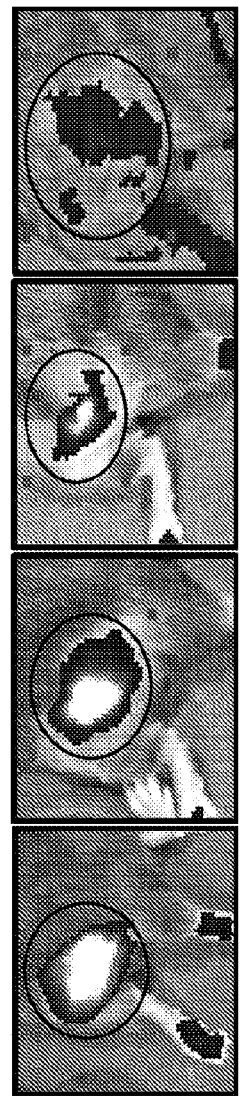
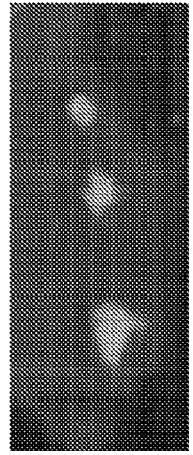
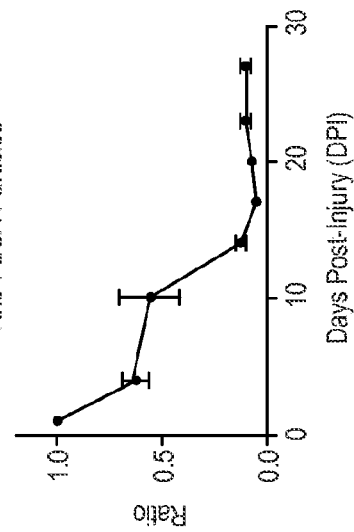
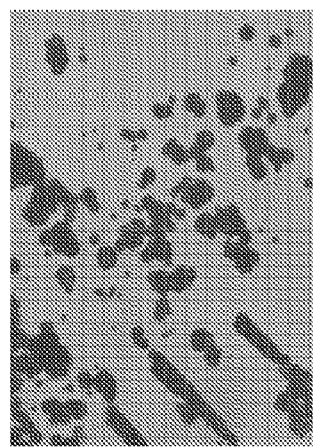
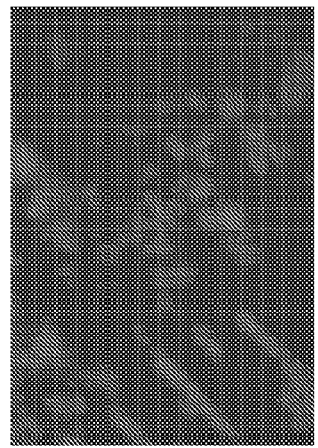
FIG. 10A  FIG. 10B  FIG. 10C  FIG. 10D

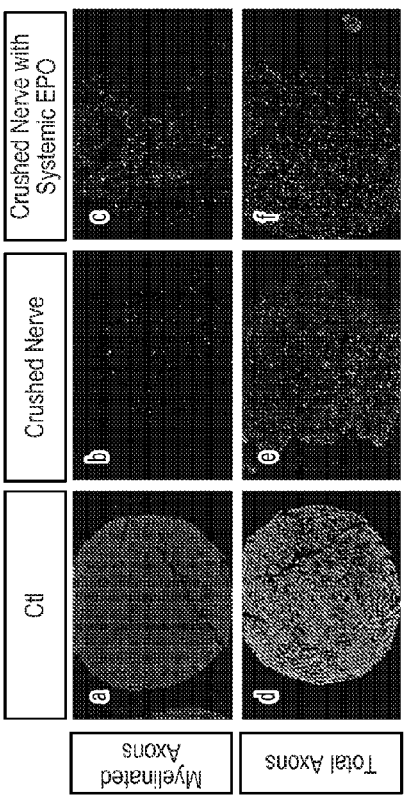
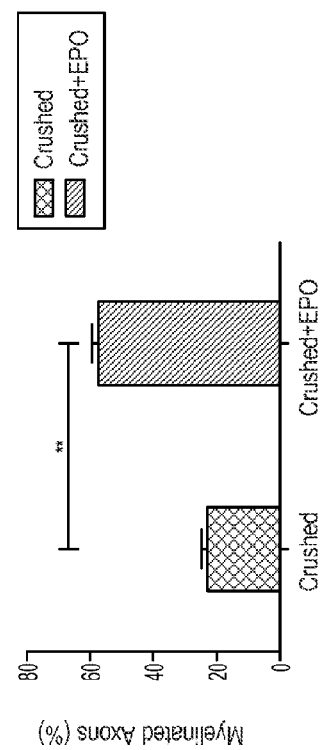
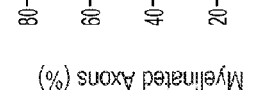
FIG. 14A
FIG. 14B
FIG. 14C

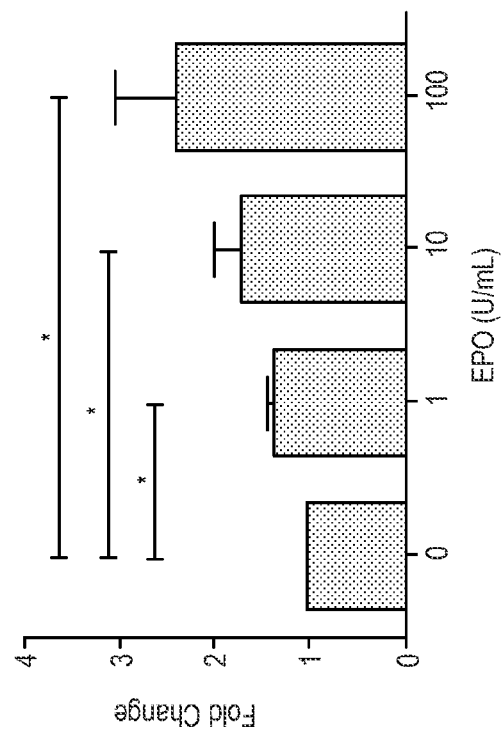
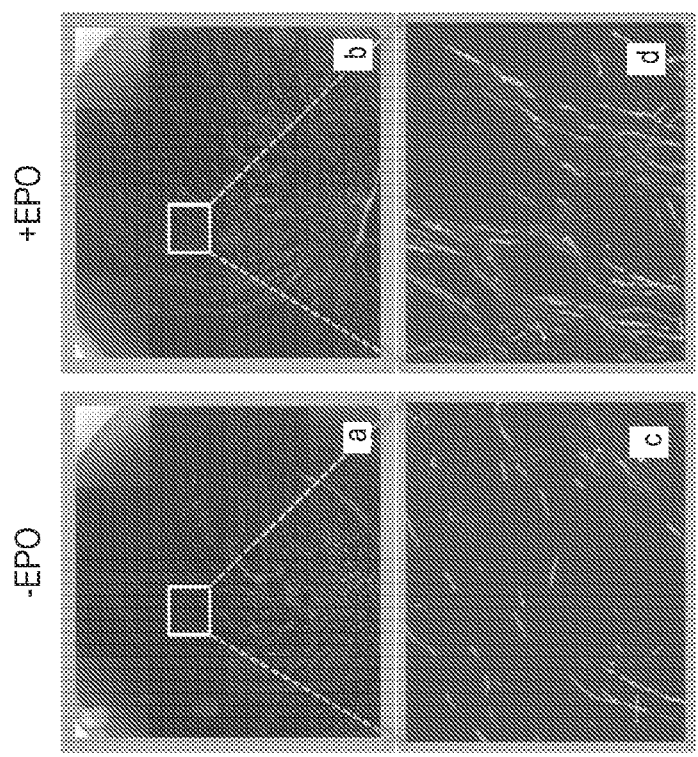
FIG. 15A
FIG. 15B

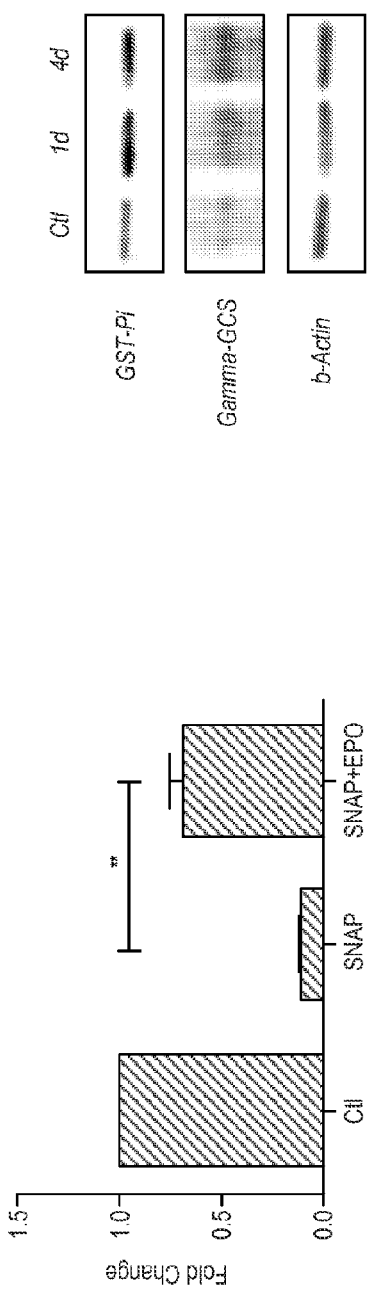
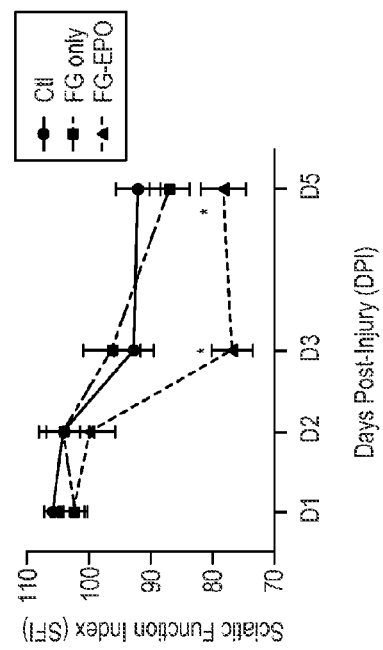
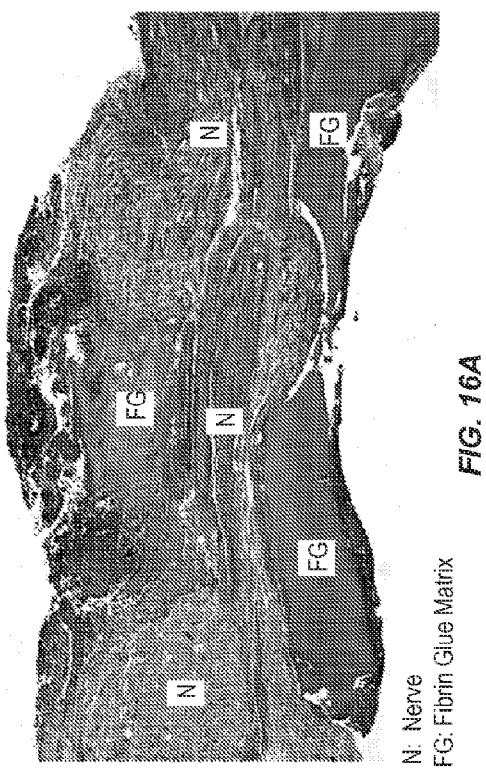
FIG. 15C
FIG. 15D
FIG. 16A
FIG. 16B

COMPOSITION AND METHODS FOR THE TREATMENT OF PERIPHERAL NERVE INJURY

CROSS-REFERENCE TO RELATED APPLICATIONS

This application claims priority to provisional Patent Application No. 61/793,360, filed Mar. 15, 2013, and is incorporated by reference herein in its entirety.

STATEMENT AS TO RIGHTS UNDER FEDERALLY SPONSORED RESEARCH

This invention was made with government funding under Grant No. K08 AR060164-01A from the National Institutes of Health. The government has certain rights in the invention.

BACKGROUND

Chronic compression neuropathy, also referred to as nerve compression syndrome or entrapment neuropathy, is a condition caused by pressure on a single nerve. This condition is currently treated through the surgical release of the compressive tissue. However, the response to surgical treatment is unpredictable, especially in nerves deemed to have un-recordable conduction velocity. Systemic administration for this indication has not been attempted. Thus, while repair of transected or severed nerves has been a major focus of study, little has been done to improve the repair of crushed or compressed peripheral nerves.

BRIEF SUMMARY

Provided herein are methods of treating a peripheral nerve injury in a subject. The methods include administering to the subject, at or near the site of the peripheral nerve injury, an effective amount of a composition comprising an agent that promotes remyelination of the peripheral nerve. The composition is formulated for slow release of the agent in an amount that treats the peripheral nerve injury in the subject.

Also provided are methods of determining whether a peripheral nerve injury has a capacity for recovery. The methods include selecting a subject with a peripheral nerve injury, administering to the subject a first dose of a composition comprising an agent that promotes remyelination and is formulated for slow release at or near the sight of the peripheral nerve injury, and detecting after the first dose one or more characteristics of peripheral nerve recovery. The presence of one or more characteristics of peripheral nerve recovery indicates the peripheral nerve injury has a capacity for recovery. The absence of characteristics of peripheral nerve recovery indicates a peripheral nerve injury without a capacity for recovery.

BRIEF DESCRIPTION OF THE DRAWINGS

FIG. 2A is a graph showing treatment with 4-AP on day 3 and FIG. 2B is a graph showing treatment with 4-AP on day 5 after crush injury.

FIGS. 4A, 4B, 4C, and 4D are a table and electron micrograph images relating to 4-AP encapsulated in PLGA. FIG. 4A is a table showing data related to the particle fabrication of compositions comprising 4-AP encapsulated in PLGA under varying conditions. FIGS. 4B, 4C, and 4D show scanning electron micrograph images of compositions comprising 4-AP encapsulated in PLGA as prepared according to conditions in FIG. 4A. FIG. 4B is an image showing homogenization with speeds $1^{st}$ 17,500 rpm and $2^{nd}$ 9500 rpm with reduced fragile structure and some holes on the surface of the spheres and a lower loading capacity of 4-AP. FIG. 4C is an image showing the removal of organic solvent from the double emulsion solution through a vacuum causes holes on the spheres and extremely low loading efficiency. FIG. 4D is an image showing homogenization with speeds $1^{st}$ 21,000 rpm and $2^{nd}$ 13,500 rpm for 90 seconds on each step and evaporation of organic solvent in a chemical hood with good air flow can produce even, firm microparticles with 200-500 nm in diameter loaded with 4-AP.

FIG. 9A is an image of the PLGA particles encapsulating 4-AP. FIG. 9B is a graph showing 4-AP is continuously released from the 4-AP encapsulated PLGA particles for 28 days in vitro. FIG. 9C is an image of a film comprising 4-AP encapsulated in PLGA. FIG. 9D is a graph showing 4-AP was released more quickly during the first 7 days from 4-AP PLGA films than from 4-AP PLGA particles. FIG. 9E is a graph showing that 4-AP PLGA films soaked in PBS for 24 days and moved into fresh PBS solution were able to continue to release 4-AP for 14 days.

FIGS. 10A, 10B, 10C, and 10D show PLGA particles labeled with rhodamine and implanted into mice around the sciatic nerve remained at or near the site of implantation and continued to release 4-AP at the site of implantation over time. FIG. 10A is an image showing the morphology of rhodamine labeled 4-AP PLGA particles in vitro. FIG. 10B are images of a mouse leg implanted with rhodamine labeled 4-AP PLGA particles monitored by an In Vivo Imaging System (IVIS). FIG. 10C is a graph of the quantitative data of the fluorescence intensity captured in FIG. 10B as detected by the IVIS. FIG. 10D is an image of 4-AP PLGA particles retrieved from mice 21 days after treatment indicating the particles remained at the site of implantation for at least 21 days.

FIG. 13A is a representative picture of crushed sciatic nerve in mice. FIG. 13B are representative photographs of the foot position of the sham-surgery group (panel a), saline-treated mouse (panel b), and systemic EPO-treated mouse (panel c) 7 days after the surgical crush injury. FIG. 13C is a graph showing the effect on SFI improvement with single systemic administration of EPO through subcutaneous injection. (unpaired t-test, n=5, p<0.05). FIG. 13D shows intraperitoneal application of 100 μg of 4-Aminopyridine transiently improves SFI after the surgery. Because of the short-term bioactivity of 4-AP in vivo, the SFI improved only briefly.

FIGS. 14A, 14B, and 14C are images and a graph showing EPO supported preservation of myelin within crushed nerves. FIG. 14 A is an image of the immunofluorescent staining of destroyed myelin sheath at the injured site 7 days post-injury. FIG. 14B is an image showing immunofluorescent staining of myelinated axons and total axons in the cross sections of sciatic nerves 7 days post-injury. Representative images of the cross sections of the sciatic nerves (a, d: healthy nerve; b, c, e, f: crushed nerve). FIG. 14C is a graph showing the ratio of the number of myelinated axon to total axons of crushed sciatic nerves with or without EPO administration. (unpaired t-test, n=3, three animals for each set, p<0.01).

FIGS. 15A, 15B, 15C, and 15D are images and graphs showing EPO promoted myelin formation and protected myelination under nitric oxide (NO) Stress. FIG. 15A is an image showing immunoncytochemical staining of myelin in co-culture stained with anti-myelin basic protein (MBP) mouse monoclonal antibody. FIG. 15 B is a graph showing quantitative result of myelination in the presence of different concentrations of EPO. EPO enhances myelin-formation in a dose-dependent manner. (unpaired t-test, n=4, p<0.05) FIG. 15 C is a graph showing myelination in the presence of 100 μM of SNAP during the myelination-induction process with or without 100 U/mL EPO treatment. (unpaired t-test, n=4, p<0.01) FIG. 15D is a gel image of immunoblotting of glutathione S-transferase and gamma-glutamylcysteine synthetase levels in Schwann cells with 100 U/mL EPO treatment.

FIGS. 16A and 16B are an image and graph showing local EPO treatment via fibrin glue vehicle improves motor function. FIG. 16A is an image showing the crushed sciatic nerve tightly attached with fibrin glue matrix 3 days after surgery. FIG. 16B is a graph showing 0.5 U EPO-loaded fibrin glue implant improved SFI significantly in 3 days. (unpaired t-test, n=5, p<0.05).

DETAILED DESCRIPTION

Figure 1A:
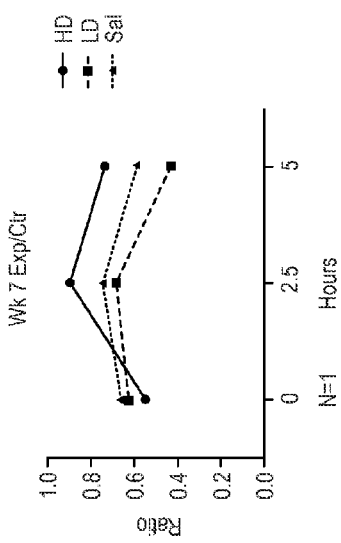
FIGS. 1A, 1B and 1C show graphs of nerve conduction velocity at 7 weeks (FIG. 1A), 9 weeks (FIG. 1B) and 12 weeks (FIG. 1C) of compression and treatment with high dose 4-AP (HD), low dose of 4-AP (LD), and saline (Sal). 4-AP was administered IP in a single dose as a bolus.

The present disclosure is directed to methods of treating a peripheral nerve injury in a subject. The methods include administering to the subject, at or near the site of the peripheral nerve injury, an effective amount of a composition comprising an agent that promotes remyelination of the peripheral nerve. The composition is formulated for slow release of the agent and the amount of the agent released treats the peripheral nerve injury in the subject. Administration includes placing the composition in proximity to a therapeutic target, e.g., the peripheral nerve; thus, optionally, allowing for administration of the agent in concentrations higher than those that could be achieved for systemic administration or at concentrations that would result in one or more adverse side effects if administered systemically.

Also provided herein are methods of determining whether a peripheral nerve injury has a capacity for recovery. The method includes selecting a subject with a peripheral nerve injury, administering to the subject a first dose of a composition comprising an agent that promotes remyelination formulated for slow release at or near the sight of the peripheral nerve injury, and detecting after the first dose one or more characteristics of peripheral nerve recovery. The presence of one or more characteristics of peripheral nerve recovery indicates the peripheral nerve injury has a capacity for recovery, and the absence of a characteristic of peripheral nerve recovery indicates a peripheral nerve injury without a capacity for recovery. Optionally, the recovery is partial recovery (i.e., not to control, asymptomatic levels).

The detecting step is performed within three, four, five, six, seven, eight, nine, or ten days after administration of the first dose of the agent. Optionally, the detecting step is performed within three, four, or five days after administration of the first dose of the agent.

Optionally, the first dose is administered by insertion, implantation or injection into the subject, at or near the site of the peripheral nerve injury. The first dose can be administered as described herein, for example, in a sustained delivery device. Optionally, the sustained delivery device is an implant or osmotic pump. Optionally, the implant is a nerve cuff. Optionally, the implant is a bioerodible or reservoir-based implant. Optionally, the implant is a bead or film containing the agent that promotes remyelination.

The methods optionally further include administering to the subject one or more agents for treating the peripheral nerve injury, if the peripheral nerve injury has a capacity for recovery. Optionally, the one or more agents comprise a second dose of a composition comprising EPO, wherein the composition is formulated to slowly release EPO. Optionally, the agents are selected from the group consisting of forskolin, colforsin, glial growth factor-2, a myelin binding antibody, 4-AP, a derivative of 4-AP and combinations thereof.

Methods for detecting a characteristic of peripheral nerve function or evaluating injuries of peripheral nerves are known. Examples of methods for detecting a characteristic of peripheral nerve recovery can be carried out by physical exam, electromagnetic fields, functional nerve electrical stimulation, electromyography or nerve conduction study. Characteristics of improved nerve function include improved nerve conduction, reduced pain, improved sensation, improved motor function, sweating, and the like. Determining a characteristic of peripheral nerve activity, refers to comparing the presence or amount of the characteristic in an individual to its presence or amount in persons known to suffer from or in persons known to be free of nerve injury, and assigning an increased or decreased probability of recovery of the peripheral nerve injury to an individual based on the characteristic of the peripheral nerve activity.

As discussed above, the present disclosure relates to compositions and methods related to administering a therapeutically effective amount of a compound for the purpose of treating acute or chronic peripheral nerve neuropathy or injury. The present disclosure contemplates the use of formulations and/or drug-delivery techniques for the extended and sustained delivery of pharmaceutical compositions, specifically, compositions comprising relatively fast-acting compounds with a short half-life inside the body or compositions with adverse systemic side effects.

Provided herein is a method of treating a peripheral nerve injury in a subject. The method includes administering to the subject, at or near the site of the peripheral nerve injury, an effective amount of a composition comprising an agent that promotes remyelination of the peripheral nerve. The composition is formulated for slow release of the agent and the amount released treats the peripheral nerve injury in the subject. Types of nerve injuries suitable for treatment in the provided methods by promoting remyelination include but are not limited to a stretched nerve, compressed nerve, a traumatized nerve and a crushed nerve. Optionally, the nerve injury is caused by surgery. Optionally, the peripheral nerve injury is associated with traumatic injury, carpel tunnel syndrome or sciatica. Preferably, the peripheral nerve injury is not a transected nerve or severed nerve.

Types of nerve injuries suitable for the provided methods include but are not limited to a stretched nerve, compressed nerve, pinched nerve, a traumatized nerve and a crushed nerve. Optionally, the nerve injury is caused by surgery. Optionally, the peripheral nerve injury is associated with traumatic injury, carpel tunnel syndrome or sciatica. Preferably, the peripheral nerve injury is not a transected nerve or severed nerve. The terms transected nerve and severed nerve refer to a nerve that has been cut, for example, such that all axons of the nerve have been transected or severed. As used herein, peripheral nerve injuries include nerve injuries in which axons continue to extend through the injury site.

As demonstrated herein, such peripheral nerve injuries can be repaired by treatment with a re-myelination agent, i.e., an agent that promotes remyelination. Further, prior to or upon initiation of a treatment regimen, such injuries can be determined to have a capacity for recovery by exposing the nerve injury to an agent that promotes remyelination and evaluating the nerve injury for a characteristic of recovery.

Suitable agents for use in the provided methods for promoting remyelination include, but are not limited to erythropoietin (EPO), forskolin or a derivative thereof (e.g., colforsin), 4-aminopyridine (4-AP) or a derivative thereof, glial growth factor-2, myelin binding antibodies, and combinations thereof.

Optionally, the agent is erythropoietin (EPO) or an active variant or derivative thereof. EPO is an endogenous 30.4-kDa hematopoietic glycoprotein originally identified for its role in erythropoiesis, regulating red blood cell production by preventing apoptosis of erythroid progenitor cells. EPO is clinically used for a variety of purposes including to correct anemia arising from chronic renal failure and cancers in adults. As used throughout, methods referring to the use of EPO or erythropoietin include the use of recombinant erythropoietin, synthetic erythropoietin, chemically modified erythropoietin, darbepoieten, glycosylated erythropoietin, EPO-alpha, EPO-beta, EPO-delta, EPO-zeta, and EPO-omega and combinations thereof. Methods of making and using EPO as well as its variants and derivatives are known and described in, for example, U.S. Pat. Nos. 5,955,422; 5,547,933; 5,441,868; 5,618,698; 5,756,349; and 5,621,080, the contents of each of which are incorporated herein by reference in their entireties. Further, EPO is commercially available from a variety of sources including Amgen (Thousand Oaks, Calif.), Hoffmann-LaRoche (Basel, Switzerland) and Shire Pharmaceuticals Group PLC (St. Helier, Jersey). Optionally, 0.01 U/kg to 5000 U/kg of EPO is administered to the subject.

Optionally, the agent is 4-Aminopyridine (4-AP), which is a compound used in the treatment of systemic neurodegenerative disorders, such as multiple sclerosis (MS). The compound is a potassium channel blocker. Therefore, 4-AP can allow function to continue in nerves that suffer from chronic demyelinating disorders. Treatment with 4-AP has been examined in intravenous applications and in oral formulations, for example, in a formulation comprising 4-AP powder in a gelatin-based capsule, which generally affords rapid peak plasma concentrations shortly after dosing. Such treatments produce maximum plasma concentration in about 1 hour, with a plasma half-life of 3-4 hours. The rapid release and short half-life characteristics of 4-AP can make maintaining effective plasma levels difficult without producing relatively high concentration peaks following each respective dose. Further, the dosage of 4-AP is confined by toxicities which occur at high dose levels. Accordingly, spikes in concentration may result in undesirable side effects, such as seizures and trembling.

Extended release formulations comprising 4-AP include tablets, capsules, or granules for oral use. See, e.g., U.S. Publication Nos. 2011/0166189 and 2012/0164078. However, extended release formulations of 4-AP have generally targeted the treatment of systemic conditions such as MS. 4-AP has not been used in the treatment of traumatic or chronic peripheral nerve injuries. Further, formulations of 4-AP have been used to afford a therapeutically effective plasma concentration of 4-AP on the order of hours, for example 6 to 12 hours, and not on the order of days, which would be required to effectively treat injuries related to acute or chronic compression neuropathy. Thus, the provided methods advantageously allow for local, sustained release of the 4-AP at or near the site of the nerve injury, optionally, in concentrations that result in undesirable side effects if administered systemically.

4-Aminopyridine has the structure depicted in FIG. 4, and is also known as fampridine, 4-pyridinamine; 4-pyridylamine, or pyridin-4-amine. Optionally, the derivative of 4-aminopyridine contemplated is 3,4-diaminopyridine (3,4-DAP), having the structure depicted in FIG. 4, which is also known as amifampridine. The compound 4-aminopyridine or derivative thereof, such as amifampridine, may be present in the composition in the form of a physiologically acceptable salt, such as in combination with a physiologically acceptable anion, as is well known in the art. Optionally, the 4-AP or derivative thereof is provided in an amount of at least one microgram for at least one day at or near the site of the peripheral nerve injury.

Optionally, the agent is forskolin or a derivative thereof. Optionally, the derivative of forskolin is colforsin. Forskolin also referred to as coleonol is a labdane diterpene produced by the Indian *Coleus* plant (*Coleus forskohlii*). Forskolin is commonly used to raise levels of cyclic AMP (cAMP) for research purposes. However, forskolin and derivatives thereof are being explored for medicinal uses, for example, as a vasodilator and in the treatment of cancer. Forskolin, its derivatives, and methods of making and using forskolin and derivatives thereof are known and described in, for example, U.S. Pat. Nos. 5,804,596; and 5,350,864; and U.S. Publication No. 2011/0077292, the contents of each of which are incorporated herein by reference in their entireties. Further, forskolin and its derivatives are commercially available, for example, from Sigma Aldrich (St. Louis, Mo.) and Abcam plc (Cambridge, U.K.).

Optionally, the agent is glial growth factor-2 (GGF2), an isoform of neuregulin-1. Neuregulins are involved in cell-cell signaling and organogenesis in nerve, muscle, epithelia, and other tissues. GGF2 and methods of making and using GGF2 are known and described in, for example, U.S. Pat. Nos. 5,530,109; 5,716,930; and 7,037,888; and U.S. Publication No. 2013/0345131, the contents of each of which are incorporated herein by reference in their entireties. Further, glial growth factor-2 is commercially available, for example, from Acorda Therapeutics, Inc. (Ardsley, N.Y.).

Optionally, the agent is a myelin binding antibody. As used herein, the term antibody refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Antibodies may include antibodies that have been modified or mutated at one or more amino acid positions to improve or modulate a desired function of the antibody (e.g., glycosylation, expression, antigen recognition, effector functions, antigen binding, specificity, etc.). Optionally, the myelin binding antibody is a recombinant human monoclonal IgM antibody. Optionally, the antibody is rHIgM22. rHIgM22 (also known as rsHIgM22, sHIgM22 and LYM 22), is described in, for example, Ciric et al., J. Neuroimmunol. 146:153-161 (2004); Howe et al., Neurobiol. Dis. 15:120-131 (2004); and U.S. Publication No. 2007/0086999, and is commercially available, for example, from Acorda Therapeutics, Inc. (Ardsley, N.Y.).

Optionally, the agent is provided as a pharmaceutically acceptable salt. As used herein, the language "pharmaceutically acceptable salt" refers to a salt of the administered compounds prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

Provided herein are compositions comprising one or more of the agents that promote remyelination. The provided compositions are, optionally, suitable for formulation and administration in vitro or in vivo. Suitable carriers and excipients and their formulations are described in Remington: The Science and Practice of Pharmacy, 22d Edition, Loyd et al. eds., Pharmaceutical Press and Philadelphia College of Pharmacy at University of the Sciences (2012).

Optionally, the compositions comprise a pharmaceutically acceptable carrier. By pharmaceutically acceptable is meant a material, e.g., carrier or excipient, that is not biologically or otherwise unacceptably undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject. As used herein, the term pharmaceutically acceptable carrier means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be acceptable in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, pharmaceutically acceptable carrier also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The pharmaceutically acceptable carrier may further include a pharmaceutically acceptable salt of the compound useful within the invention. Other additional ingredients that may be included in the pharmaceutical compositions used in the practice of the invention are known in the art and described, for example in Remington: The Science and Practice of Pharmacy (2012), which is incorporated herein by reference.

Optionally, the composition may comprise a fibrin glue, a biocompatible polymer or hydrogel or a combination thereof. Optionally, the composition comprises one or more elements, e.g., one or more polymers and one or more hydrogels. By way of example, the composition may comprise a polymer embedded in the fibrin glue. Optionally, the agent is encapsulated in the polymer or hydrogel such that the agent is slowly released in the body to at least one portion of the peripheral nervous system. Optionally, the agent is dispersed throughout the polymer or hydrogel in such a manner to result in slow, sustained release as the polymer or hydrogel degrades inside the body. The agent may be uniformly dispersed, or non-uniformly dispersed in the polymer hydrogel. Optionally, the agent may be only partially encapsulated by the polymer or hydrogel. Optionally, the composition comprises poly-L-lactic acid-co-glycolic acid (PLGA). Optionally, the composition may comprise a polymerized fibrin sealant or adhesive (e.g. TISSEEL fibrin sealant) that may be used to delay the release of the agent at the site of nerve injury.

The term biodegradable includes polymers, compositions and formulations, such as those described herein, that are intended to degrade during use. Biodegradable polymers typically differ from non-biodegradable polymers in that the former may be degraded during use. Optionally, such use involves in vivo use, such as in vivo therapy. Alternatively, such use involves in vitro use. In general, biodegradation involves the degradation of a biodegradable polymer into its component subunits, or digestion, e.g., by a biochemical process, of the polymer into smaller, non-polymeric subunits. Two types of biodegradation may generally be identified. For example, biodegradation may involve cleavage of bonds (whether covalent or otherwise) in the polymer backbone. In such biodegradation, monomers and oligomers typically result, and even more typically, such biodegradation occurs by cleavage of a bond connecting one or more of subunits of a polymer. Further, biodegradation may involve cleavage of a bond (whether covalent or otherwise) internal to side chain or that connects a side chain to the polymer backbone. For example, a therapeutic agent or other chemical moiety attached as a side chain to the polymer backbone may be released by biodegradation. Optionally, at least one type of biodegradation may occur during use of a polymer. As used herein, the term biodegradation encompasses all known types of biodegradation.

The terms biocompatible polymer, polymer, polymeric material, hydrogel, and the like are used interchangeably herein, and refer to a polymeric material that does not cause inflammatory or immune response in the body. Non-limiting examples of biodegradable biocompatible polymers are: polyglycolide or polyglycolic acid (PGA); polylactide or polylactic acid (PLA); poly-L-lactic acid (PLLA); poly-D/L-lactic acid with polyglycolic acid (PDLLA-co-PGA); poly-L-lactic acid-co-glycolic acid (PLGA); PDLLA with bioactive glass; PLGA with bioactive glass; poly-L-lactic acid with β-tricalcium phosphate (PLLA-TCP); poly-L-lactic acid with hydroxyapatite (PLLAHA); polydioxanone (PDS); polyethylene glycol (PEG); poly(ε-caprolactone) (PCL); polycaprolactone (PCL) with alginate; polyhydroxybutyrate (PHB); polycarbonate (PC); N-vinyl pyrrolidone copolymers; polyorthoester; chitosan; poly(2-hydroxyethylmethacrylate) (PHEMA); hyaluronic acid and hydrogels.

As used herein, the terms incorporated and encapsulated refer to a therapeutic agent and a polymeric composition, such as a composition disclosed herein. These terms include incorporating, formulating or otherwise including such agent into a composition which allows for sustained release of such agent in the desired application. The terms may contemplate any manner by which a therapeutic agent or other material is incorporated into a polymer matrix, including for example, attached to a monomer of such polymer (by covalent or other binding interaction) and having such monomer be polymerized to give a polymeric formulation; distributed throughout the polymeric matrix; appended to the surface of the polymeric matrix (by covalent or other binding interactions); encapsulated inside the polymeric matrix, and the like. The term co-incorporation or co-encapsulation refers to the incorporation of a therapeutic agent or equivalent and at least one other therapeutic agent or equivalent in a subject composition.

Figure 3:
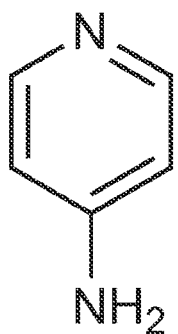
FIG. 3 is a schematic of 4-aminopyridine (4-AP) and a derivative thereof, 3,4-diaminopyridine.
Figure 3:
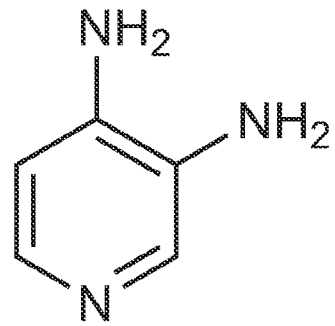

The polymer or hydrogel of the composition degrades inside the body to release the encapsulated agent in a slow, consistent manner. As the polymeric material undergoes degradation inside the body, it generates non-toxic degradation products, which may be eliminated by the body as such or metabolized into one or more non-toxic molecules. Optionally, compositions comprising the agent at least partially encapsulated in polymeric material are formed into beads, films, or some other shape, as would be understood by a person of ordinary skill in the art. The size of each individual bead, film, or other shape is of a suitable size for implantation or other form of administration, as would be understood by a person of ordinary skill in the art. Further, the size of each individual bead, film, or other shape may be substantially consistent, or there may be a distribution of different sizes of the respective shape. By way of example, referring now to FIG. 3, a scanning electron micrograph is shown that depicts a composition wherein beads comprising 4-AP encapsulated in PLGA are shown. Optionally, the beads can be implanted, ingested, or otherwise placed inside the body in some way, such that the agent is administered locally or systemically in a sustained-release manner.

Optionally, the composition may be in the shape of a film. The composition may be in the shape of a solid block or brick. The film or block can be used without further processing, or the film or brick can be shaped for a specific application. Further, the composition may be initially formed into a desired shape using 3D printing technology. For example, the composition can be formed into the structure of a tube that is suitable for wrapping around a nerve; a grooved surface that can cradle a nerve; or a structure comprising a hole or other feature that would be suitable for suturing or adhering to tissue or other biological structures. Further, the composition may be in the form of putty, i.e. a malleable material that could be formed into the desired structure at the time of implantation.

Optionally, the polymer comprises a synthetic polymer or copolymer prepared from at least one of the group of monomers consisting of acrylic acid, methacrylic acid, ethyleneimine, crotonic acid, acrylamide, ethyl acrylate, methyl methacrylate, 2-hydroxyethyl methacrylate, lactic acid, glycolic acid, ε-caprolactone, acrolein, cyanoacrylate, bisphenol A, epichlorhydrin, hydroxyalkylacrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-amino-benzyl-styrene, sodium styrene sulfonate, sodium 2-sulfoxyethyl methacrylate, vinyl pyridine, aminoethyl methacrylates, 2-methacryloyloxy-trimethylammonium chloride, N,N'-methylenebisacrylamide-, ethylene glycol dimethacrylates, 2,2'-(p-phenylenedioxy)-diethyl dimethacrylate, divinylbenzene, and triallylamine, methylenebis-(4-phenyl-isocyanate). Optionally, the substrate comprises polydimethylsiloxane elastomer (PDMS).

A variety of polymers from synthetic and/or natural sources can be used. For example, lactic or polylactic acid or glycolic or polyglycolic acid can be utilized to form poly(lactide) (PLA) or poly(L-lactide) (PLLA) nanofibers or poly(glycolide) (PGA) nanofibers. The composition can also be made from more than one monomer or subunit thus forming a co-polymer, terpolymer, etc. For example, lactic or polylactic acid and be combined with glycolic acid or polyglycolic acid to form the copolymer poly(lactide-co-glycolide) (PLGA). Other copolymers include poly(ethylene-co-vinyl) alcohol). Optionally, the composition can comprise a polymer or subunit which is a member selected from an aliphatic polyester, a polyalkylene oxide, polydimethylsiloxane, polyvinylalcohol, polylysine, and combinations thereof. Optionally, the composition can comprise two different polymers or subunits which are members selected from an aliphatic polyester, a polyalkylene oxide, polydimethylsiloxane, polyvinylalcohol, polylysine, and combinations thereof. Optionally, the composition comprises three different polymers or subunits which are members selected from an aliphatic polyester, a polyalkylene oxide, polydimethylsiloxane, polyvinylalcohol, polylysine, and combinations thereof. Optionally, the aliphatic polyester is linear or branched. Optionally, the linear aliphatic polyester is a member selected from lactic acid (D- or L-), lactide, poly(lactic acid), poly(lactide) glycolic acid, poly(glycolic acid), poly(glycolide), glycolide, poly(lactide-co-glycolide), poly(lactic acid-co-glycolic acid), polycaprolactone and combinations thereof. Optionally, the aliphatic polyester is branched and comprises at least one member selected from lactic acid (D- or L-), lactide, poly(lactic acid), poly(lactide) glycolic acid, poly(glycolic acid), poly(glycolide), glycolide, poly(lactide-co-glycolide), poly(lactic acid-co-glycolic acid), polycaprolactone and combinations thereof which is conjugated to a linker or a biomolecule. Optionally, the polyalkylene oxide is a member selected from polyethylene oxide, polyethylene glycol, polypropylene oxide, polypropylene glycol and combinations thereof.

By way of example, the composition may be formed from functionalized polyester graft copolymers. The functionalized graft copolymers are copolymers of polyesters, such as poly(glycolic acid) or poly(lactic acid), and another polymer including functionalizable or ionizable groups, such as a poly(amino acid). Optionally, polyesters may be polymers of a-hydroxy acids such as lactic acid, glycolic acid, hydroxybutyric acid and valeric acid, or derivatives or combinations thereof. The inclusion of ionizable side chains, such as polylysine, in the polymer has been found to enable the formation of more highly porous particles, using techniques for making microparticles known in the art, such as solvent evaporation. Other ionizable groups, such as amino or carboxyl groups, may be incorporated, covalently or non-covalently, into the polymer to enhance porosity. For example, polyaniline could be incorporated into the polymer. These groups can be modified further to contain hydrophobic groups capable of binding load molecules.

Optionally, the composition can include one or more of the following: polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly(ethylene glycol), poly(ethylene oxide), poly(ethylene terephthalate), poly(vinyl acetate), polyvinyl chloride, polystyrene, polyvinyl pyrrolidone, pluronics, polyvinylphenol, saccharides (e.g., dextran, amylose, hyalouronic acid, poly(sialic acid), heparans, heparins, etc.); poly (amino acids), e.g., poly(aspartic acid) and poly(glutamic acid); and copolymers thereof.

Optionally, the composition can include one or more of the following: peptide, saccharide, poly(ether), poly(amine), poly(carboxylic acid), poly(alkylene glycol), such as poly (ethylene glycol) ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), polysialic acid, polyglutamate, polyaspartate, polylysine, polyethyeleneimine, biodegradable polymers (e.g., polylactide, polyglyceride and copolymers thereof), polyacrylic acid.

Optionally, the composition may be formed using emulsion processing techniques. The emulsion processing technique may comprise the steps of adding ingredients, for example a solution of 4-AP and a polymer in a solvent, to water, then using homogenization equipment to mix and/or disperse the ingredients to form beads, microspheres, or other particles. The homogenization step may comprise a primary or first homogenization step, and a secondary homogenization step. The emulsion process may further comprise the steps of extracting and/or drying the particles comprising the composition. Optionally, the composition may be formed by emulsion solvent diffusion techniques (see for example, Chu and Lu, ed., Biomaterials Fabrication and Processing Handbook, CRC press (2008)), which is herein incorporated by reference in its entirety). Such emulsion solvent diffusion techniques may comprise the production of particles via oil-in water or water-in-oil-in-water techniques. Further the techniques may comprise a single emulsion or double emulsion process. However, the composition may be produced using any process for making compositions suitable for drug delivery applications, as would be understood by a person with ordinary skill in the art.

Optionally, the provided compositions are inserted, implanted or injected into the subject. Optionally, the composition is administered by insertion, implantation or injection into the subject at or near the site of the peripheral nerve injury. Thus, the compositions can be provided locally at the site of an acute or chronic peripheral nerve injury. Optionally, the beads, films, or other form of slow-release mechanism can be placed in relatively close proximity to an injured nerve in the peripheral nervous system, such that the agent is administered in a sustained-release manner to the injured nerve. Optionally, the compositions are placed in relatively close proximity to a nerve prior to, or concurrent with, a surgical procedure, for example by way of image guidance. Optionally, the nerve can be uninjured, such that the placement of the composition near the nerve serves to administer the composition in a preventive or prophylactic manner. By relatively close proximity includes but is not limited to abutting the site of injury or within 1-2 centimeters of the site of injury. As the distance from the site of injury is increased, the concentration of the agent released must be higher to compensate for the distance, however, so that the pharmacologically effective dose reaches the site of the injury.

The agents and compositions may be administered by delivery devices that are known to those of skill in the art. Thus, the composition can be administered by a sustained delivery device or inert delivery vehicle. Optionally, as described above, the sustained delivery device is an implant or osmotic pump. Optionally, the implant is a nerve cuff. Optionally, the implant is a bioerodible or reservoir-based implant. Sustained delivery devices in which the compositions and/or agents can be incorporated are known. Sustained delivery or controlled-release systems may include, for example, an infusion pump which may be used to administer the agent or composition to specific locations. Optionally, using such a system, the agent is administered in combination with a biodegradable, biocompatible polymeric implant that releases the agent over a controlled period of time at a selected site. These include, for example, hydropropylmethyl cellulose, other polymer matrices, gels, permeable membranes, osmotic systems, multilayer coatings, microparticles, liposomes, microspheres, or the like, or a combination of any of the above to provide the desired release profile in varying proportions.

Thus, the disclosed compositions can be applied to an implantable device such as a nerve cuff, and the like, to enhance the compatibility and/or performance or function of an implantable device in an implant site. The disclosed compositions can be used to coat the implantable device. For example, the disclosed compositions could be used to coat the rough surface of an implantable device to enhance the compatibility of the device by providing a biocompatible smooth surface which reduces the occurrence of abrasions from the contact of rough edges with the adjacent tissue. The disclosed compositions can also be used to enhance the performance or function of an implantable device.

According to the methods taught herein, the subject is administered an effective amount of one or more of the agents provided herein. The terms effective amount and effective dosage are used interchangeably. The term effective amount is defined as any amount necessary to produce a desired physiologic response (e.g., promoting nerve function). Effective amounts and schedules for administering the agent may be determined empirically by one skilled in the art. The dosage ranges for administration are those large enough to produce the desired effect in which one or more symptoms of the injury or disorder (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the injury or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products. Optionally, the 4-AP or derivative thereof is provided in an amount of at least one microgram for at least one day at or near the site of the peripheral nerve injury. Optionally, 0.01 U/kg to 5000 U/kg of EPO is administered to the subject.

In the provided methods of treatment, additional therapeutic agents can be used that are suitable to the disease being treated. Thus, in some embodiments, the provided methods of treatment further comprise administering a second therapeutic agent to the subject. Suitable additional therapeutic agents include, but are not limited to, therapeutic agent is selected from the group consisting of steroids and anti-inflammatory agents. Non-limiting examples of steroids include methylprednisolone, dexamethasone, prednisone, and any combination thereof. Any corticosteroid, glucocorticoid, and the like may be used in the provided methods. Optionally, the anti-inflammatory agent is a non-steroidal anti-inflammatory drug (NSAID). Non-limiting examples of a NSAID include salicylates (e.g. aspirin), propionic acid derivatives (e.g. ibuprofen or naproxen), acetic acid derivatives (e.g. indomethacin), oxicam derivatives (e.g. piroxicam), and Fenamates (e.g. menafemic acid). The choice of agent and dosage can be determined readily by one of skill in the art based on the given disease being treated.

Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

Throughout this disclosure, various aspects can be presented in a range format. It should be understood that the description in range format is merely for convenience and brevity and should not be construed as an inflexible limitation. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein the terms treatment, treat, or treating refers to a method of reducing the effects of an injury or disorder or symptom of the injury or disorder. Thus in the disclosed method, treatment can refer to a 10%, 20%, 30%, 40%, 50%, 60%, 70%, 80%, 90%, or 100% reduction in the severity of an established injury or disorder or symptom of the injury or disorder. For example, a method for treating an injury or disorder is considered to be a treatment if there is a 10% reduction in one or more symptoms of the injury or disorder in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the injury, disorder, or symptoms of the injury or disorder.

As used herein, the terms prevent, preventing, and prevention of an injury or disorder refers to an action, for example, administration of a therapeutic agent, that occurs before or at about the same time a subject begins to show one or more symptoms of the injury or disorder, which inhibits or delays onset or exacerbation of one or more symptoms of the injury or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

As used throughout, subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder (e.g., nerve damage, like nerve compression). The term patient or subject includes human and veterinary subjects.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a composition is disclosed and discussed and a number of modifications that can be made to a number of molecules including the composition are discussed, each and every combination and permutation of the composition, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

A number of embodiments have been described. Nevertheless, it will be understood that various modifications may be made. Accordingly, other embodiments are within the scope of the claims below.

EXAMPLES

Example 1

4-Aminopyridine for the Treatment of Peripheral Nerve Injury

Figure 1B:
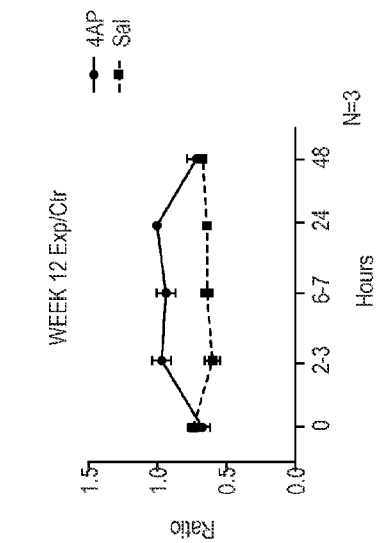
Figure 1C:
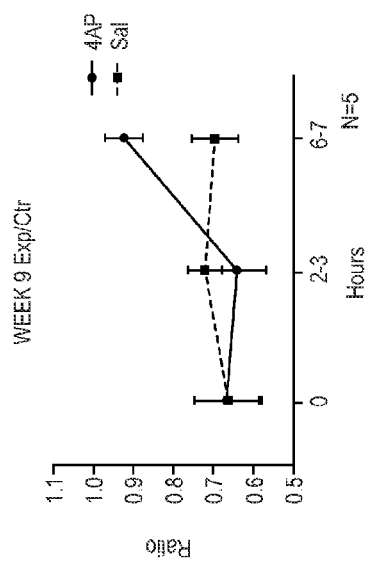

The concept that 4-AP may have a role in the treatment of compressed nerves emanates from data showing that the conduction velocity of compressed nerves can respond strongly to pharmacologic treatment with this agent. In FIG. 1, three small pilot experiments demonstrate that at various time points, 4-AP treatment can render the function of nerves as measured by their improved conduction velocity. In all three experiments, performed on mice with compression mediated by a sleeve around the nerve for different numbers of weeks, strong effects of 4-AP administration was seen. The ratio of the conduction velocity of the compressed nerve divided by the corresponding contralateral uninjured nerve in these animals shows that recovery is possible, albeit transient (bottom right panel) in these animals. Therefore, 4-AP may be used locally or systemically for the treatment of chronic compression injury.

Figure 2B:
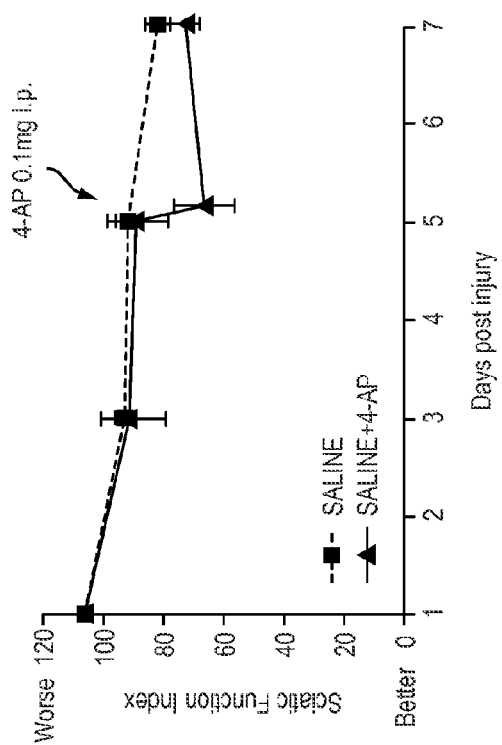
FIGS. 2A and 2B show graphs of the sciatic nerve index 1-7 days post injury in the presence and absence of 4-AP.
Figure 2A:
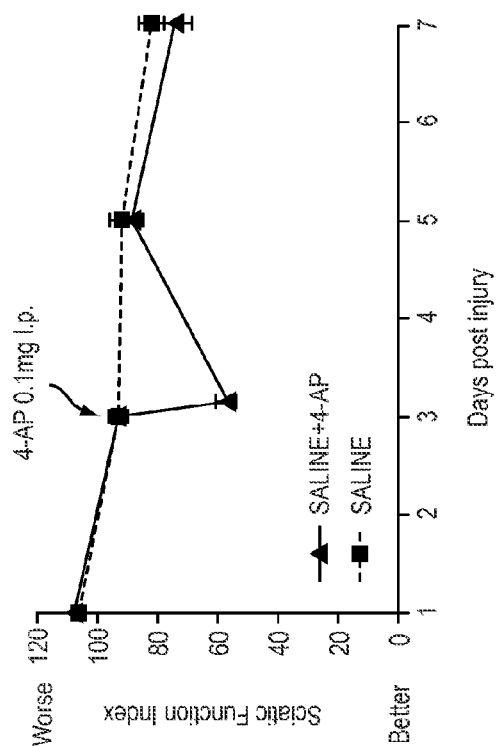

There are also possible effects of the 4-AP on nerve injuries suffered more acutely. Acute nerve injury is both common and difficult to treat. One type of acute peripheral nerve injury with a murine model available for study is the sciatic nerve crush injury model in mice and rats. In this model, the nerve is crushed with a variable amount of force which creates a measurable functional deficit in gait. This deficit is measured using a sciatic function index which is an accepted and validated measure of the functional effects of the injury. This measure and this model were used to show that 4-AP, administered systemically, could ameliorate the effects of an acute peripheral nerve crush injury. As can be seen in FIG. 2, the effects of 4-AP can be evidenced even days after injury to the sciatic nerve. In each case, the desired large improvement in the function of the animals gait is demonstrated.

Figure 5:
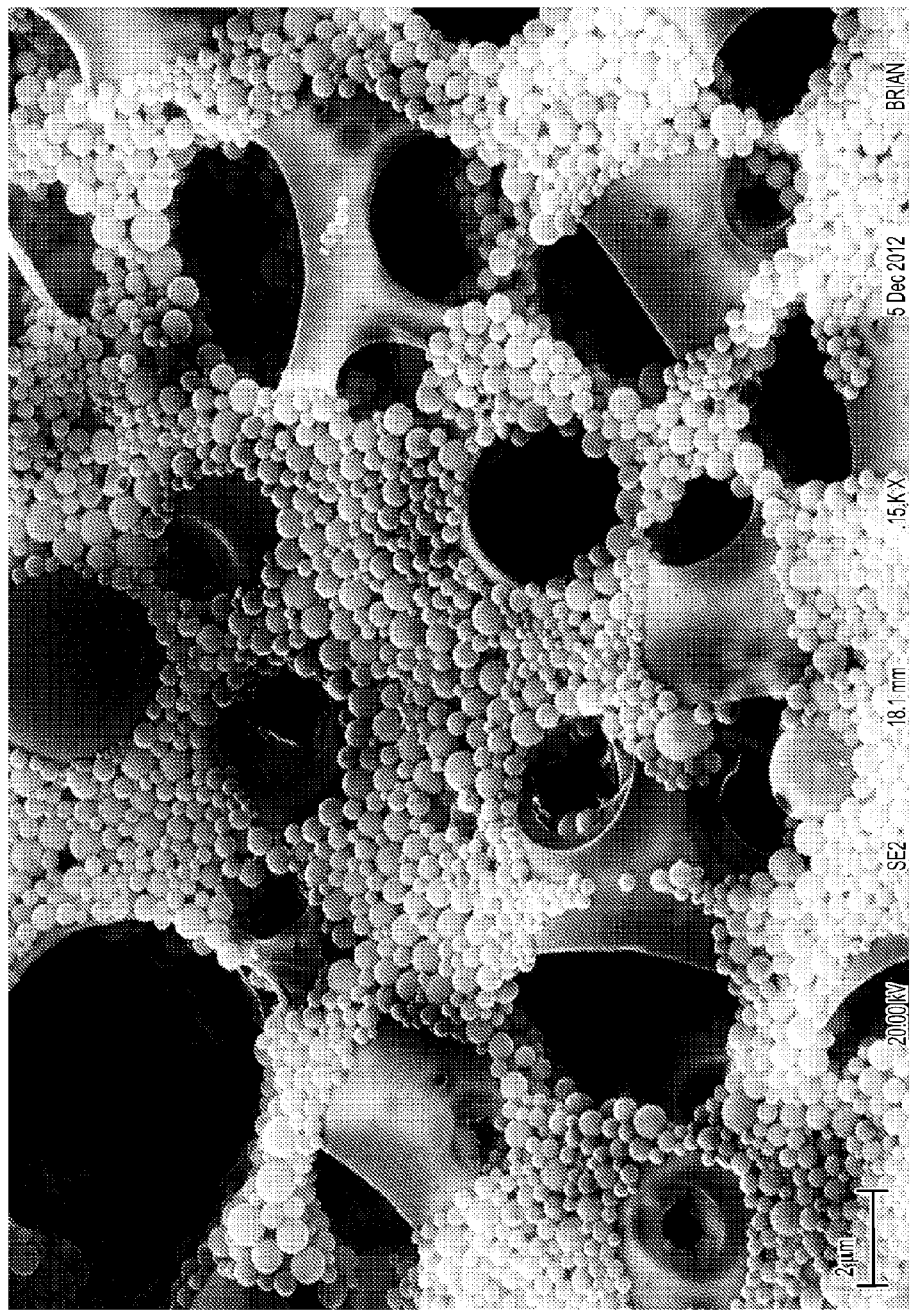
FIG. 5 is a scanning electron micrograph (SEM) image showing beads comprising 4-AP encapsulated in PLGA. A water/oil/water double emulsion with 50:50 PLGA produces even size and solid forms of microparticles 200-500 nm in diameter loaded with 4-AP. The beads shown were produced using an emulsion process characterized by a primary homogenization step at 21,500 rpm for 90 seconds and a secondary homogenization step at 13,500 for 90 seconds.
Figure 6:
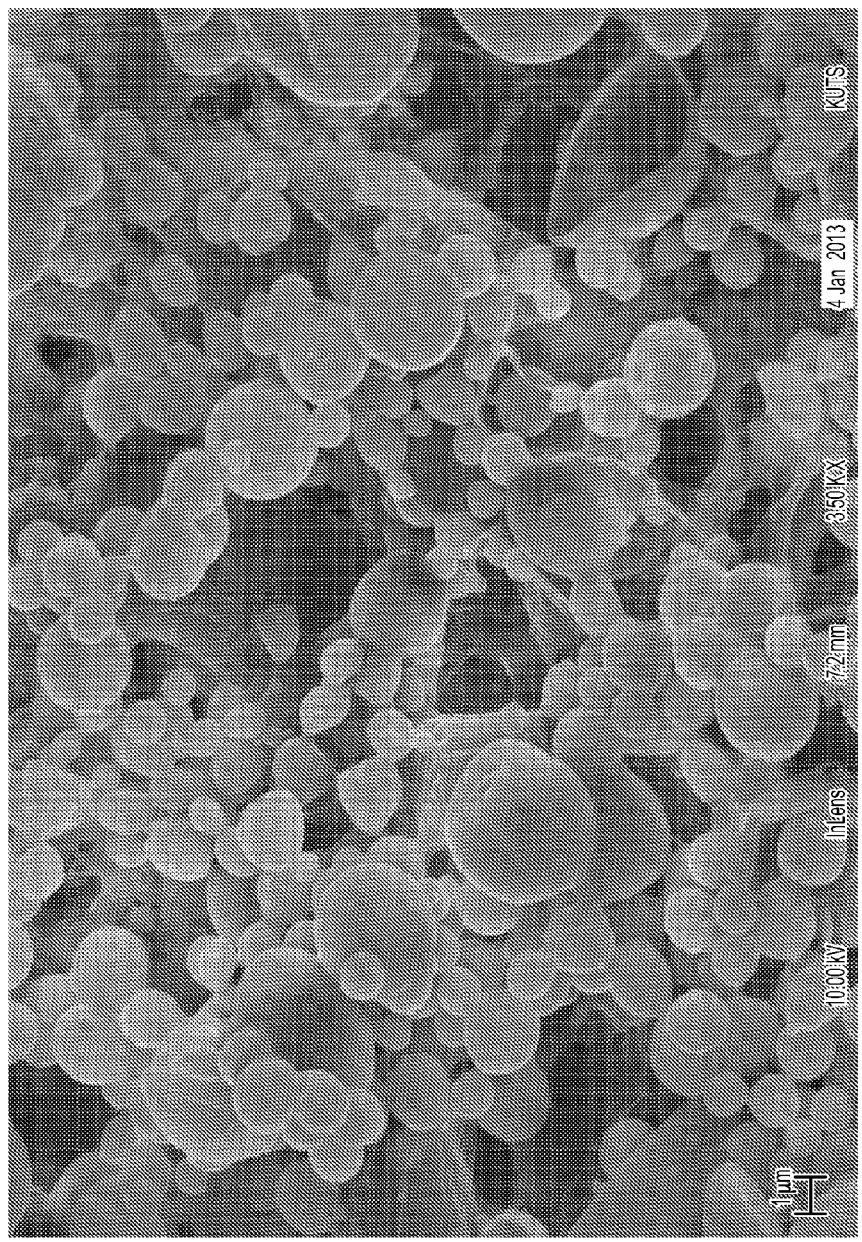
FIG. 6 is a SEM image relating to beads comprising 4-AP encapsulated in PLGA. The beads shown were produced using an emulsion process characterized by a primary homogenization step at 21,500 rpm for 30 seconds and a secondary homogenization step at 13,500 for 30 seconds. The beads produced in this case have fragile structure with some surface holes on the spheres and lower loading capacity.
Figure 7:
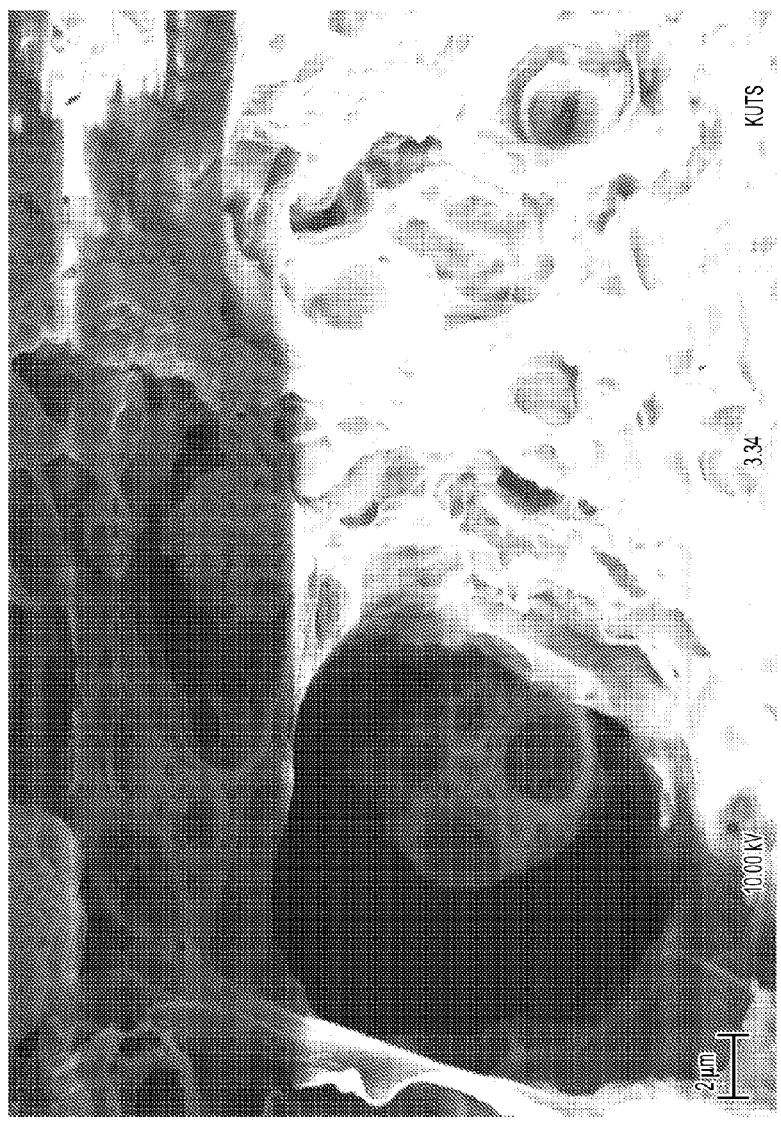
FIG. 7 is a scanning electron micrograph image of a composition comprising 4-AP encapsulated in PLGA. The structure shown was produced using an emulsion process characterized by a primary homogenization step at 13,500 rpm for 30 seconds and a secondary homogenization step at 9,500 for 30 seconds and included attempted removal of organic solvent from the double emulsion solution through vacuum. The result shows holes in the surface of the spheres and low loading capacity.

To further evaluate the effects of 4-AP, 4-AP was encapsulated in PLGA to obtain a slow release formulation that could be used locally at the site of implantation, e.g., the site of nerve injury. FIGS. 4A, 4B, 4C, and 4D are a table and electron micrograph images relating to such encapsulation. A water/oil/water double emulsion was used to produce the PLGA microparticles. There are three major variables to affect the morphology and the firmness of microparticles: (i) the speed of homogenization, (ii) time length of each homogenization step, and (iii) the evaporation of organic solvent. FIG. 4A is a table showing data related to the particle fabrication of compositions comprising 4-AP encapsulated in PLGA varying these conditions. FIGS. 4B, 4C, and 4D show scanning electron micrograph images of compositions comprising 4-AP encapsulated in PLGA as prepared according to conditions in FIG. 4A. FIG. 4B is an image showing homogenization with speeds 1st 17,500 rpm and 2nd 9500 rpm with reduced fragile structure and some holes on the surface of the spheres and a lower loading capacity of 4-AP. FIG. 4C is an image showing the removal of organic solvent from the double emulsion solution through a vacuum causes holes on the spheres and extremely low loading efficiency. FIG. 4D is an image showing homogenization with speeds 1st 21,000 rpm and 2nd 13,500 rpm for 90 seconds on each step and evaporation of organic solvent in a chemical hood with good air flow can produce even, firm microparticles with 200-500 nm in diameter loaded with 4-AP. As shown in FIG. 5 a water/oil/water double emulsion with 50:50 PLGA produces even size and solid forms of microparticles 200-500 nm in diameter loaded with 4-AP. The beads shown were produced using an emulsion process characterized by a primary homogenization step at 21,500 rpm for 90 seconds and a secondary homogenization step at 13,500 for 90 seconds. In contrast, beads or particles produced using an emulsion process characterized by a primary homogenization step at 21,500 rpm for 30 seconds and a secondary homogenization step at 13,500 for 30 seconds resulted in particles with fragile structure with some surface holes on the spheres and lower loading capacity (FIG. 6). Further, particles produced using an emulsion process characterized by a primary homogenization step at 13,500 rpm for 30 seconds and a secondary homogenization step at 9,500 for 30 seconds, which also included attempted removal of organic solvent from the double emulsion solution through vacuum resulted in holes in the surface of the spheres and low loading capacity (FIG. 7). Thus, provided is a method of producing suitable 4-AP encapsulated PLGA particles or beads.

Figure 8:
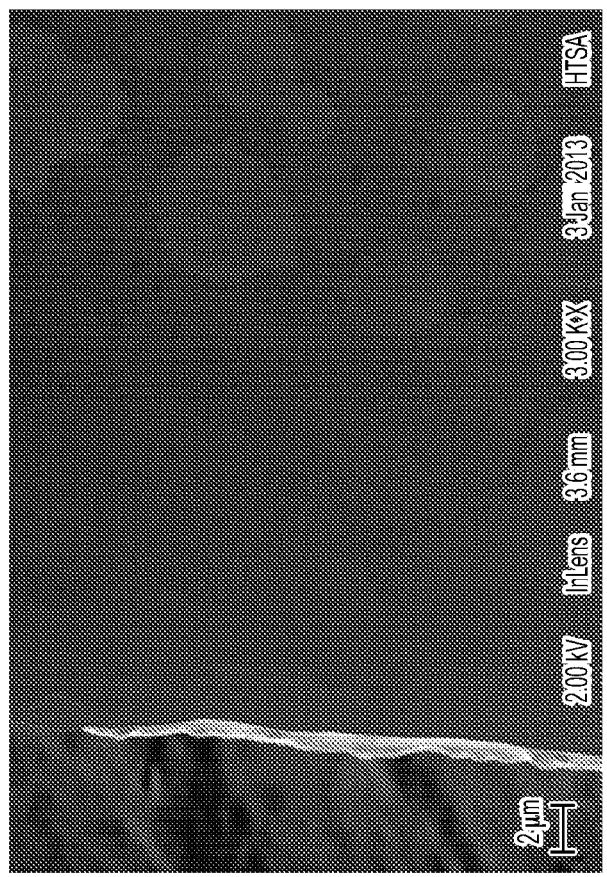
FIG. 8 is a scanning electron micrograph image showing a film comprising 4-AP encapsulated in PLGA. The film shown was produced using a solvent casting method characterized by dissolving 3 mg of 4-AP and 50 mg of PLGA in 1 mL dichloromethane. The solution was then dried under vacuum to form the film-like structure. The white line is the edge of the PLGA film and to the right of the line shows the film structure under 3000× magnification showing the film has a smooth surface.

In order to determine if 4-AP can be formulated for slow release in a different manner, a film comprising 4-AP encapsulated in PLGA was made. The film was produced using a solvent casting method characterized by dissolving 3 mg of 4-AP and 50 mg of PLGA in 1 mL dichloromethane. The solution was then dried under vacuum to form the film-like structure. The white line is the edge of the PLGA film and to the right of the line shows the film structure under 3000× magnification showing the film has a smooth surface (FIG. 8).

Figure 9A:
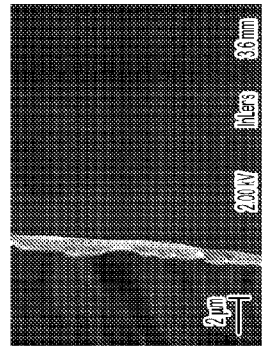
FIGS. 9A, 9B, 9C, 9D, and 9E are images and graphs showing the release profile of encapsulated 4-AP from PLGA vehicles in vitro in PBS on rocker with 150 rpm at room temperature.
Figure 9B:
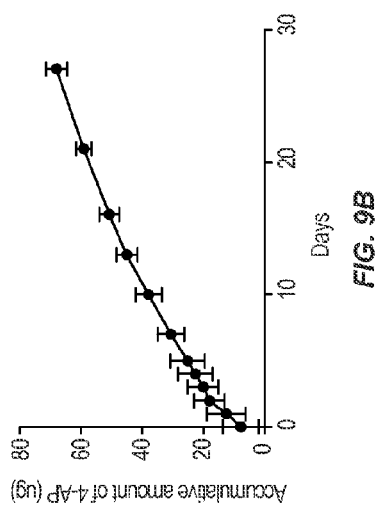
Figure 9C:
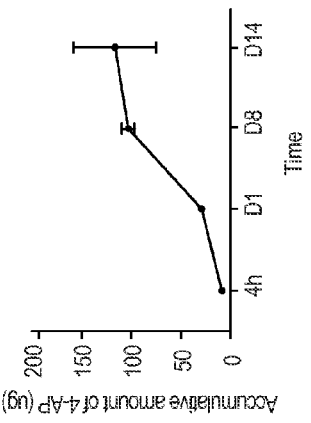
Figure 9D:
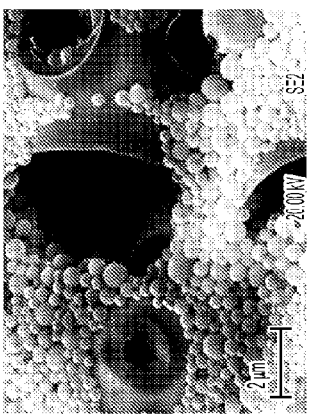
Figure 9E:
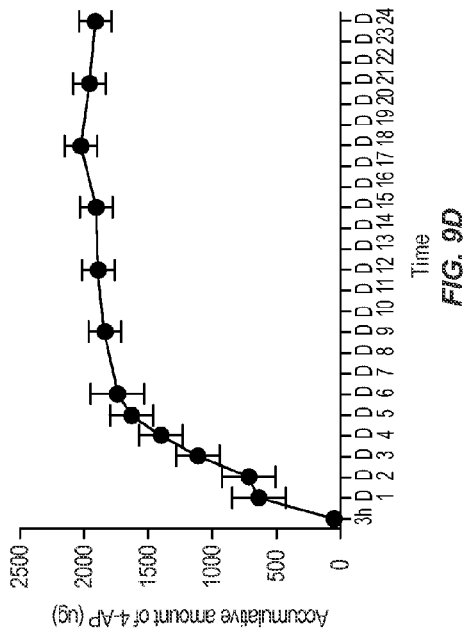

In order to test the release profile of 4-AP PLGA particles and 4-AP PLGA film, the release of 4-AP from these formulations was assessed in vitro and in vivo. FIG. 9A is an image of the PLGA particles encapsulating 4-AP. FIG. 9B is a graph showing 4-AP is continuously released from the 4-AP encapsulated PLGA particles for 28 days in vitro. FIG. 9C is an image of a film comprising 4-AP encapsulated in PLGA. FIG. 9D is a graph showing 4-AP was released more quickly during the first 7 days from 4-AP PLGA films than from 4-AP PLGA particles. However, FIG. 9E is a graph showing that 4-AP PLGA films soaked in PBS for 24 days and moved into fresh PBS solution were still able to continue to release 4-AP for another 14 days.

To further evaluate the 4-AP PLGA particles, the particles were labeled with rhodamine and implanted into mice around the sciatic nerve. FIG. 10A is an image showing the morphology of rhodamine labeled 4-AP PLGA particles in vitro. The 4-AP PLGA particles remained at or near the site of implant and released 4-AP over a period of over 20 days (FIGS. 10A, 10B, and 10C). FIG. 10D shows that 4-AP PLGA particles remained at the site of implantation for at least 21 days.

Figure 11:
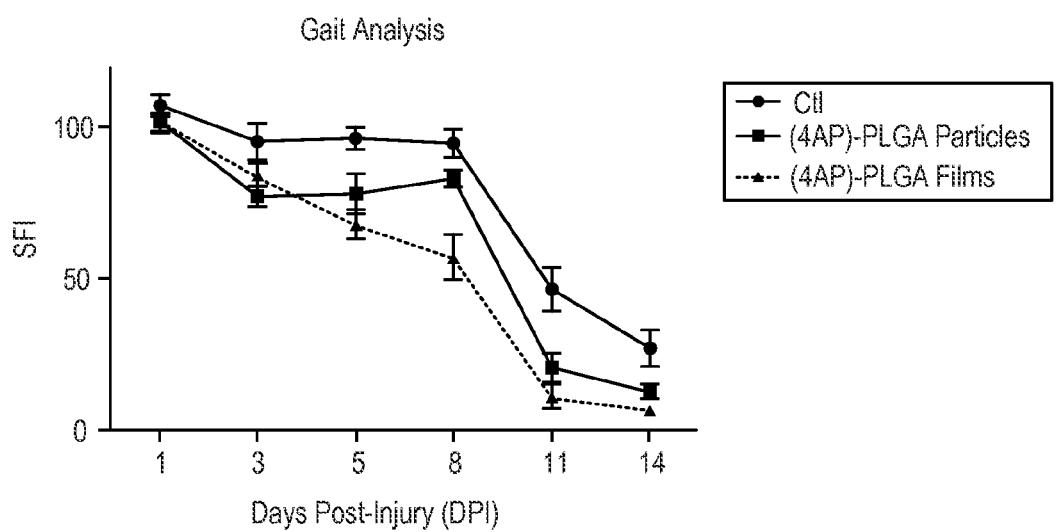
FIG. 11 is a graph showing the motor function analysis of a crushed sciatic nerve with or without treatment of 4-AP PLGA particles.
Figure 12:
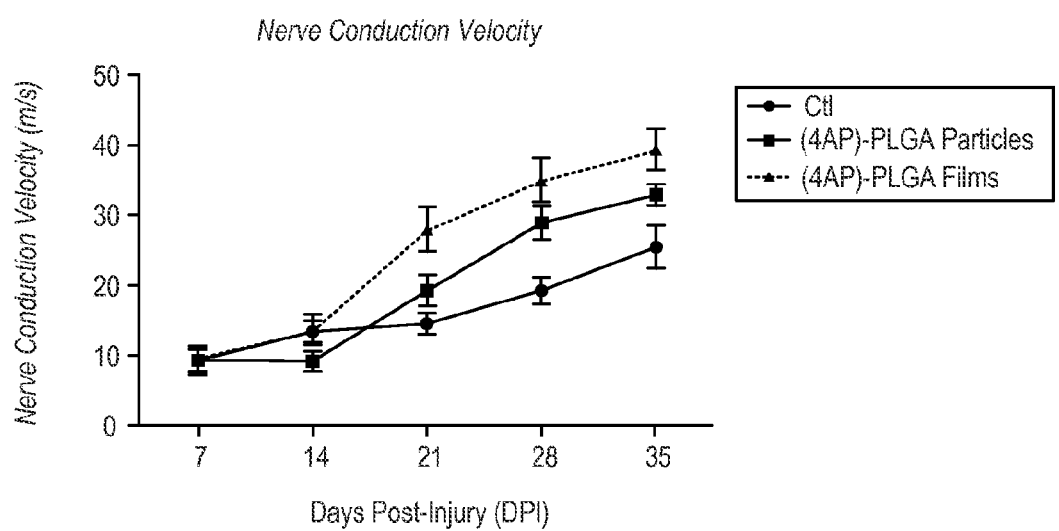
FIG. 12 is a graph showing nerve conduction velocity as measured by electromyography on animals with crushed sciatic nerve injury with or without treatment of 4-AP PLGA particles.

To further assess the function of slow release formulations of 4-AP in vivo, gait analysis and nerve conduction velocity were determined in mice with a crushed sciatic nerve implanted with 4-AP PLGA particles or 4-PLGA films at or near the site of nerve injury. FIG. 11 is a graph showing the motor function analysis of a crushed sciatic nerve with or without treatment of 4-AP PLGA particles. FIG. 12 is a graph showing nerve conduction velocity as measured by electromyography on animals with crushed sciatic nerve injury with or without treatment of 4-AP PLGA particles. Local, sustained and slow release of 4-AP significantly improved walking ability as early as three days after surgery as well as significantly improved nerve conduction velocity.

Example 2

Erythropoietin (EPO) for the Treatment of Peripheral Nerve Injury

Improving the course of recovery from peripheral nerve injuries is of critical importance. As described herein, it was found that systemic EPO administration maintained a higher extent of myelinated axons at the site of injury in vivo following sciatic nerve crush. In vitro, EPO treatment promotes myelin formation and protects myelination from oxidative stress in co-cultures of Schwann cells and dorsal root ganglion (DRG) neurons. For translational application to ameliorate the current limitations of using EPO in the clinic, local EPO treatment for peripheral nerve injury delivered by fibrin glue matrix was evaluated. The results described herein demonstrate the effects of EPO on myelin preservation and reformation and further provide EPO as a treatment for peripheral nerve injury. As EPO has been shown to have adverse side effects when administered systemically, the local delivery of EPO reduces the chance of such side effects. Specifically, local delivery of EPO promotes myelin preservation in peripheral nerve crush injury in vivo and also promotes and protects myelination in Schwann cell-DRG neuron co-cultures; moreover, local treatment of EPO through fibrin glue vehicle promotes the motor function recovery of animals suffering from a crush sciatic nerve injury.

Materials and Methods

Reagents And Antibodies. Recombinant human erythropoietin was obtained from Jassen Products, LP (Horsham, Pa.). Anti-protein zero (P0) and anti-neurofilament chicken monoclonal were obtained from Ayes Labs Inc. (Tigard, Oreg.) Anti-myelin basic protein (MBP) mouse monoclonal was obtained from Chemicon (Billerica, Mass.). Anti-GST-Pi monoclonal antibody was obtained from BD Bioscience (San Jose, Calif.). Anti-gamma-glutamylcysteine synthetase rabbit polyclonal was obtained from Abcam (Cambridge, England). Anti-thy1.1 (OX7) and anti-β-Actin monoclonal were obtained from Santa Cruz Biotechnology (Dallas, Tex.). Anti-fibronectin rabbit polyclonal and rabbit complement were obtained from Sigma Aldrich (St. Louis, Mo.). Tissel fibrin sealant was obtained from Baxter (Deerfield, Ill.).

Mouse Model of Peripheral Nerve Injury. All procedures were approved by the University of Rochester Committee on Animal Resources. Female 10-week-old C57BL6 mice were performed sciatic nerve crush injury on the left hindlimb and the sham-surgery on the other one. All extensive surgery procedures were as described previously (Elfar et al., *The Journal of Bone and Joint Surgery*, 90:1644-1653 (2008)). rhEPO was administered immediately at a dose of 5000 U/kg (Juul, *Acta Paediatrica* 91:36-42 (2002), Bianchi et al., *PNAS* 101:823-828 (2004), and Elfar et al., *The Journal of Bone and Joint Surgery*, 90:1644-1653 (2008)).

Sciatic Function Index (SFI) Determined by Walking Track Analysis. The assessment of motor function recovery was performed by calculating the sciatic function index (SFI). Walking track analysis was performed according to a published model that quantifies sciatic nerve function performance (de Medinaceli et al., *Exp. Neurol.* 77:634-643 (1982)). The operating procedure is extensively described previously (Elfar et al., *The Journal of Bone and Joint Surgery*, 90:1644-1653 (2008)). In brief, individual mouse footprints were obtained by painting each foot and walked down the 50 cm path in a narrow corridor lined with paper. Gaits were measured from the resulting footprints to get (1) toe spread (TS) (first through fifth toes), (2) print length (PL), and (3) intermediate toe spread (ITS) (second, third, and fourth toes) of both limbs (Gladman et al., *The Journal of Neuroscience*, 32:563-571 (2012)). All three measurements from the three most clearly inked foot prints per run were taken from the normal (N) and experimental (E) sides, and the SFI were calculated using the following formula:

$$SFI=-38.3((EPL-NPL)/NPL)+109.5((ETS-NTS)/NTS)+13.3((EIT-NIT)/NIT)-8.8$$

where E is the injured limb and N is the control limb.

Primary Schwann Cell Culture. Schwann cells were isolated from sciatic nerves of 7-day-old Sprague-Dawley rats and incubated in 1 μM anti-mitotic cytosine-β-D-arabinofuranoside (Ara-C) containing proliferating media for 3 days to eliminate fibroblasts. Afterward, complement killing was performed to further eliminate fibroblasts with anti-fibronectin, anti-Thy1.1 antibodies, and rabbit complement. Primary Schwann cells were maintained in DMEM containing 10% fetal bovine serum (FBS), 100 U/ml penicillin, 100 µg/ml streptomycin, 21 µg/ml bovine pituitary extract and 4 µM forskolin and incubated at 37° C. under humidified 5% $CO_2$ (Li et al., Glia 51:254-265 (2005)).

Dorsal Root Ganglia (DRG) Neuron Cell Culture. DRG neurons were isolated from E18 embryos of Sprague-Dawley rats and 5,000 neurons were seeded in laminin/poly-L-lysine coated 48 well plates. Primary DRG neurons were maintained in Neurobasal media supplemented with B27 containing antioxidants, 50 ng/mL NGF, and 1 µM Ara-C. 1 µM Ara-C treatment was performed three times for two days each time following two days of fresh medium without Ara-C to eliminate fibroblasts. After two weeks, DRG neurons with extensive axons were seeded with Schwann cells for myelination tests (Syed et al., The Journal of Neuroscience 30:6122-6131 (2010)).

DRG Neuron and Schwann Cell Myelinating Co-cultures. Thirty thousand (30,000) Schwann cells were plated onto the DRG neurons per well. Co-cultures were maintained in differentiation media (DMEM/F12 (1:1), 50 ng/mL NGF, 1× N2 supplement) for a week. Co-cultures were then changed to myelinating medium (MEM, 50 ng/mL NGF, 50 µg/mL ascorbic acid, 10% FBS) for two weeks. Medium was changed every two days (Syed et al., The Journal of Neuroscience 30:6122-6131 (2010)). EPO was added three times at day 6 of differentiating stage, day 1, and day 3 of myelinating stage.

Myelin Quantification. To quantify the extent of myelination in co-cultures, the total number of MBP+ myelin was counted within the whole culture well and normalized by the total cell number (DAPI+).

Local Delivery of EPO through Fibrin Glue Matrix. Required concentration of EPO was diluted in saline and added to thrombin and procoagulant protein, two components of fibrin glue, according to the ratio of 1:1:4 to make 10 µL matrix at 25° C. for local delivery onto sciatic nerve immediately after the surgery.

Results

Figure 13A:
FIGS. 13A, 13B, 13C, and 13D are images and graphs showing EPO improves sciatic functional index (SFI) in mice after crush injury with some undestroyed axons.
Figure 13B:
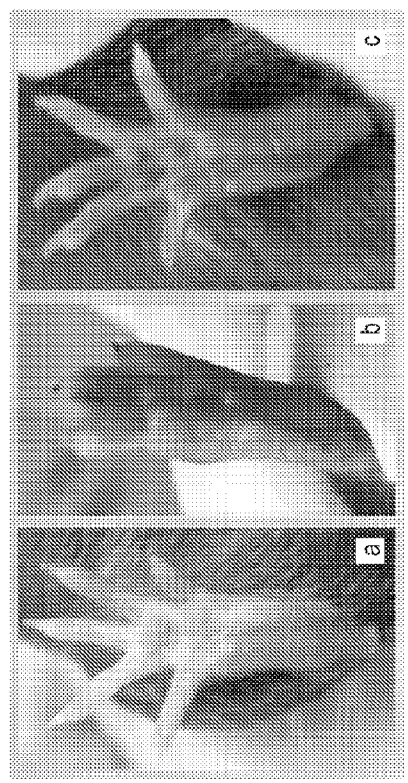

Animals with crush injuries to the sciatic nerve were treated with either single-dose subcutaneous systemic EPO (5000 U/kg) directly after injury or vehicle control. FIG. 13A shows a representative picture of the crushed sciatic nerve at surgery. Representative photographs of mouse hind limbs (FIG. 13B, panel a, sham surgery) showing normal uninjured hind limb appearance compared with panel b which shows a complete loss of normal toe spread and footprint characteristics in crush injured animal and panel c showing close-to-normal appearance with EPO treatment at seven days post-surgery.

Figure 13D:
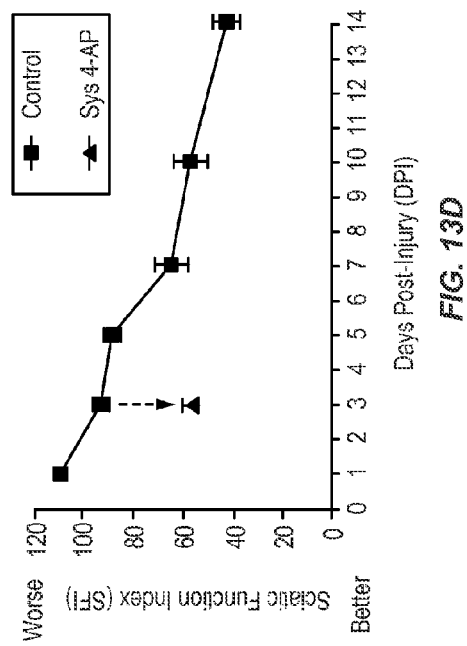
Figure 13C:
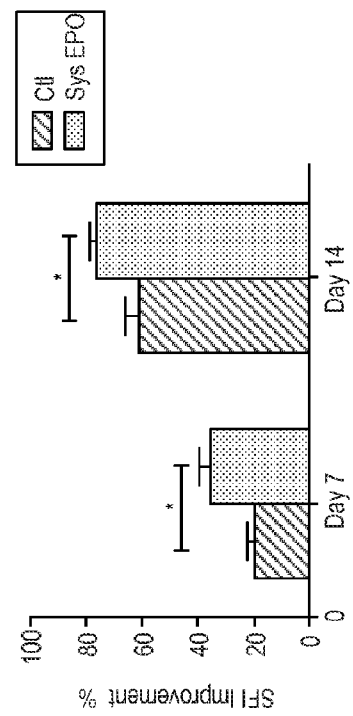

It was found that injury was associated with a severe impairment in sciatic function index (SFI) and that EPO administration was associated with statistically significant improvements in function. When SFI was determined 7 days after injury, there was an 80% reduction in function in injured animals. Mice receiving EPO showed improved function, 20% higher than in untreated animals. On day 14 after injury, there was substantial improvement in both groups. Animals treated with systemic EPO showed a more fully restored performance and the SFI was 15% more restored compared to control group at this time point. (FIG. 13C)

To work towards the underlying action by which EPO works, it was noticed that the speed of recovery in injured mice was too rapid to be attributable to axonal regeneration. 4-aminopyridine (4-AP) is a potassium channel blocker which enables demyelinated axons to conduct impulses, and thus can be used to identify injuries in which whether there exist anatomically intact but demyelinated axons. Mice receiving a sciatic nerve crush injury, performed poorly in SFI tests 3 days after injury. However, intraperitoneal administration of 4-AP produced significant transient improvement in SFI (FIG. 13D). Therefore blocking potassium channels can promote injured nerve conduction performance, indicating that some axons at the crushed site are still functionally intact but demyelinated. The effect of 4-AP raises the possibility that the benefits of EPO may be due to preservation of myelin and/or improvement of remyelination. Staining of longitudinal (FIG. 14A) and transverse (FIG. 14B, panel b) sections of crushed nerve with P0 myelin protein showed a significant loss of myelin in the crushed nerve 7 days after injury. Moreover, systemic EPO treatment directly after the crush injury was associated with a remarkable increase in the proportion of axons that were myelinated in sciatic nerves (FIG. 14B, panels b and c) without significantly altering the number of axons (FIG. 14B, panels e and f). In untreated mice only 25% of axons (neurofilament+) were associated with myelin (P0+) whereas EPO treatment raised this ratio to 60%. As such, the number of myelinated fibers available for fast nerve signal conduction was almost tripled in the EPO treated group (FIG. 14C). This data suggests that EPO tends to preserve and/or increase myelin.

To determine whether EPO enhances Schwann cell-mediated myelination directly we exposed Schwann cell-DRG neuron co-cultures to various concentrations of EPO (1, 10, 100 unit/mL of EPO). In FIG. 15A, every single short thread-like MBP+ staining cells representing a myelin formed by a single myelinating Schwann cell wrapped around the axon. EPO increased the total number of the MBP+ myelin in co-culture and was found to be dose-dependent with respect to EPO treatment (FIG. 15B).

With beneficial effects on remyelination, EPO also has been shown to have protective effects against oxidative stress. Among various oxidants, nitric oxide (NO) is known to cause hypomyelination in both CNS and PNS. To investigate the effects of EPO to reverse the deleterious influence from NO on myelin formation, Schwann cell-neuron co-cultures were exposed to NO donor: S-Nitroso-N-acetyl-DL-penicillamine (SNAP) in the presence of 100 U/mL EPO, and then Schwann cell-mediated myelination was assessed. The co-culture was exposed to 100 µM SNAP and the significant cell death was not observed, however, SNAP caused a robust decrease in baseline myelination (FIG. 15C). This suggests that Schwann cell-mediated myelination is sensitive to surrounding NO concentration. However, co-administration of EPO in SNAP-treated Schwann cell-DRG neuron co-culture notably recovered myelin formation in co-culture (FIG. 15C). Consistent with this antioxidant effect, immunoblotting analysis of glutathione S-transferase and gamma-glutamylcysteine synthetase, two proteins synthesizing antioxidant glutathione, was up-regulated after exposure to EPO (FIG. 15D) in isolated Schwann cell cultures.

The above demonstrated in vitro data suggest a latent clinical means of local delivery of EPO onto injured nerve tissue for treatment. EPO was administered directly at the site of crush injury using a clinically applicable material, specifically, a fibrin glue matrix. Such a delivery method would allow EPO to be administered at doses locally high enough to support clinical improvement without incurring side effects of systemic high dose EPO treatment. To test this rationale EPO-loaded fibrin glue was implanted onto the crushed nerve and the following motor function recovery was examined. The dosage of EPO was determined based on clinical systemic dosage, 5000 U/kg, and then converted in accordance with the ratio of body weight to sciatic nerve weight. Therefore, the amount of EPO needed for a sciatic nerve is 0.005 U. In this study, we provided 100 times higher dose based on two reasons. First, the in vitro data suggest that higher concentration of EPO exhibited remarkable positive effects on promoting myelin formation (FIG. 15B) and protecting myelination under NO stress (FIG. 15C); second, 0.5 U EPO is still far lower than the highest clinical dosage used for humans 240 U/kg (5 U/mouse) which might cause cardiovascular problems. (Peeters et al., *Annals of the Rheumatic Diseases*, 55:739-744 (1996)).

Figure 17:
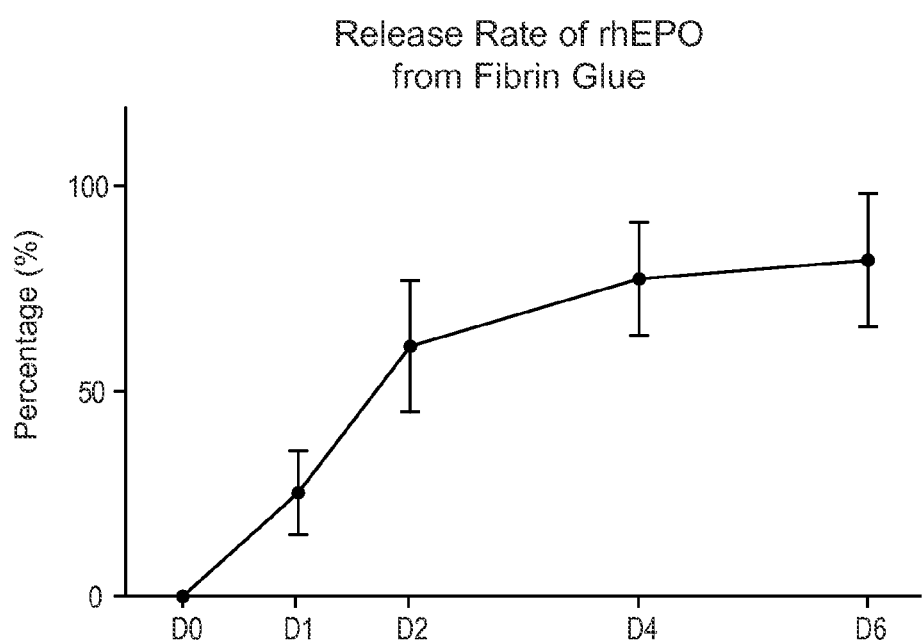
FIG. 17 is a graph showing the release profile of EPO from fibrin glue.

Either fibrin glue vehicles alone or impregnated with EPO at the site of the sciatic nerve crush injury were implanted and compared to others receiving local saline. Saline- and fibrin glue vehicle-control groups did not differ in SFI recovery (FIG. 16A). However, local EPO-treated animals showed 15% more functional improvements in SFI over control groups (FIG. 16B). The release rate of recombinant EPO from fibrin glue is shown in FIG. 17.

Taken together, the data shows that the local delivery of EPO directly at the site of injury is useful in the treatment of peripheral nerve injuries which result in totally functional deficient nerves but may spare a small population of axons. In such injuries, local treatment of EPO delivered in a fibrin glue vehicle represents a viable treatment alternative to observation. This is because EPO preserves myelin at the site of injury and speed functional motor recovery while potentially avoiding systemic side effects.

What is claimed is:

1. A method of treating or ameliorating acute peripheral nerve injury in a mammal in need thereof, the method comprising administering to the mammal a therapeutically effective amount of a biocompatible composition comprising 4-aminopyridine (4-AP) at or in close proximity to at least one portion of the injured peripheral nerve of the mammal, whereby the composition provides sustained release of the 4-AP to the at least one portion of the injured peripheral nerve of the mammal; wherein the biocompatible composition is encapsulated poly(lactic-co-glycolic acid) (PLGA) particles or film comprising 4-AP.

2. The method of claim 1, comprising further administering a steroid medicament to at least one portion of the peripheral nervous system of the mammal.

3. The method of claim 2, wherein the steroid medicament and the biocompatible composition are administered to the mammal within one hour.

4. The method of claim 3, wherein the steroid medicament and the biocompatible composition are co-formulated.

5. The method of claim 1, wherein the mammal is human.

6. The method of claim 1, wherein the 4-AP or analog thereof is in the form of a pharmacologically acceptable salt.

7. The method of claim 1, wherein the composition is administered to the carpal tunnel.

8. The method of claim 1, wherein the composition is administered through biodegradable matrix.

9. The method of claim 1, wherein administration promotes recovery of the injured peripheral nerve.

* * * * *